United States Patent [19]
Macor

[11] Patent Number: 5,886,008
[45] Date of Patent: Mar. 23, 1999

[54] 5-ARYLINDOLE DERIVATIVES

[75] Inventor: John Eugene Macor, Penfield, N.Y.

[73] Assignee: Pfizer Inc., New York, N.Y.

[21] Appl. No.: 424,357

[22] PCT Filed: Oct. 19, 1993

[86] PCT No.: PCT/US93/09790

§ 371 Date: Apr. 27, 1995

§ 102(e) Date: Apr. 27, 1995

[87] PCT Pub. No.: WO94/10171

PCT Pub. Date: May 11, 1994

Related U.S. Application Data

[63] Continuation of Ser. No. 970,758, Nov. 2, 1992, abandoned.

[51] Int. Cl.$^6$ .......................... A61K 31/44; A61K 31/52; C07D 471/02; C07D 491/02

[52] U.S. Cl. .......................... 514/303; 514/243; 514/246; 514/250; 514/249; 514/253; 514/248; 514/257; 514/266; 514/267; 514/293; 544/179; 544/183; 544/234; 544/236; 544/251; 544/256; 544/345; 544/350; 546/83; 546/118; 546/199; 548/302.1; 548/305.1

[58] Field of Search .......................... 348/305.1; 546/118; 546/83, 199; 514/243, 246, 250, 249, 253, 248, 257, 266, 267, 293, 303; 544/179, 183, 234, 236, 251, 256, 345, 350; 548/302.1

[56] References Cited

U.S. PATENT DOCUMENTS

| | | | |
|---|---|---|---|
| 4,252,803 | 2/1981 | Webb | 514/415 |
| 4,839,377 | 6/1989 | Bays et al. | 514/415 |
| 4,855,314 | 8/1989 | Oxford et al. | 514/415 |
| 4,983,622 | 1/1991 | Flaugh | 514/411 |
| 5,187,159 | 2/1993 | Greenlee et al. | 514/81 |
| 5,229,401 | 7/1993 | Effland | 514/337 |
| 5,258,385 | 11/1993 | Dodd et al. | 514/287 |
| 5,340,838 | 8/1994 | Gidda | 514/647 |
| 5,378,846 | 1/1995 | Seredenin | 544/349 |

FOREIGN PATENT DOCUMENTS

| | | |
|---|---|---|
| 0303506 | 8/1988 | European Pat. Off. . |
| 0313397 | 10/1988 | European Pat. Off. . |
| 0354777 | 8/1989 | European Pat. Off. . |
| 0457701 | 1/1991 | European Pat. Off. . |
| 0438230 | 7/1991 | European Pat. Off. . |
| 0465398 | 1/1992 | European Pat. Off. . |
| 0497512 | 8/1992 | European Pat. Off. . |
| 9118897 | 12/1991 | WIPO . |
| 9206973 | 4/1992 | WIPO . |
| 93/23396 | 11/1993 | WIPO . |
| 9323396 | 11/1993 | WIPO . |

OTHER PUBLICATIONS

W. Feniuk, et al., P.P.A. Humphrey & M. J. Perren —Br. J. Pharmacol. (1989), 96, 83–90.

P. P. A. Humphrey, et al. —Br. J. Pharmacol. (1988), 94, 1123–1132.

R. E. Hearing, et al., *J. Neuroscience*, 7, 894 (1987).

D. Hoyer, et al. *Eur. J. Pharm.*, 118, 13–23 (1985).

Supavailai, et al. *Eur. J. Pharm.*, 70, 183–93 (1981).

Muller, *Drugs of Today*, 24(a), 649–663 (1988).

*Primary Examiner*—D. Margaret M. Mach
*Attorney, Agent, or Firm*—Peter C. Richardson; Paul H. Ginsburg; Grover F. Fuller, Jr.

[57] ABSTRACT

Compounds of formula (I), wherein $R_1$ is (a), (b), (c) or (d); n is 0, 1 or 2; A, B, C and D are each independently nitrogen or carbon; $R_2$, $R_3$, $R_4$ and $R_5$ are each independently hydrogen, $C_1$ to $C_6$ alkyl, aryl, $C_1$ to $C_3$ alkyl-aryl, halogen (e.g. fluorine, chlorine, bromine or iodine), cyano, nitro, $-(CH_2)_m NR_{14}R_{15}$, $-(CH_2)_m OR_9$, $-SR_9$, $-SO_2NR_{14}R_{15}$, $-(CH_2)_m NR_{14}SO_2R_{15}$ $-(CH_2)_m NR_{14}CO_2R_9$, $-(CH_2)_m NR_{14}COR_9$, $-(CH_2)_m NR_{14}CONHR_9$, $-CONR_{14}R_{15}$, or $-CO_2R_9$; $R_2$ and $R_3$, $R_3$ and $R_4$, or $R_4$ and $R_5$ may be taken together to form a five- to seven-membered alkyl ring, a six-membered aryl ring, a five- to seven-membered heteroalkyl ring having 1 heteroatom of N, O, or S, or a five- to six-membered heteroaryl ring having H 1 or 2 heteroatoms of N, O, or S and the pharmaceutically acceptable salts thereof. These compounds are useful in treating migraine and other disorders. These compounds are useful psychotherapeutics and are potent serotonin (5-$HT_1$) agonists and benzodiazepine agonists and antagonists and may be used in the treatment of depression, anxiety, eating disorders, obesity, drug abuse, cluster headache, migraine, pain and chronic paroxysmal hemicrania and headache associated with vascular disorders, and other disorders arising from deficient serotonergic neurotransmission. The compounds can also be used as centrally acting antihypertensives and vosodilators.

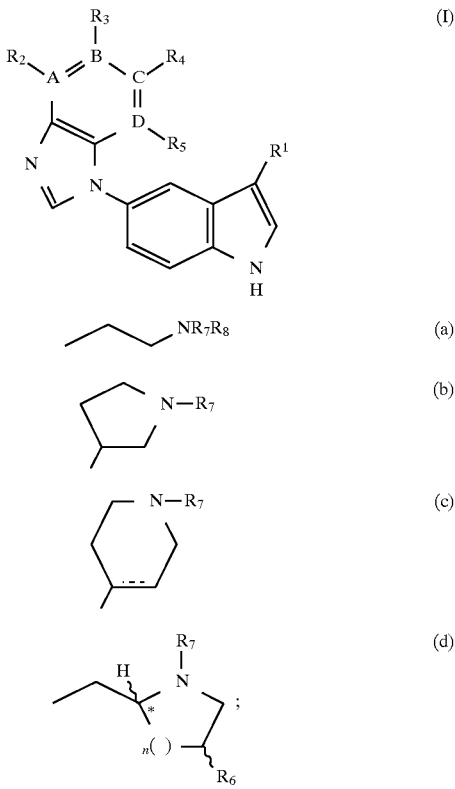

21 Claims, No Drawings

5-ARYLINDOLE DERIVATIVES

This application is a 371 of PCT/US93/09790, filed Oct. 19, 1993, which is a continuation of 07/970,758, filed Nov. 2, 1992, now abandoned.

BACKGROUND OF THE INVENTION

The present invention relates to Indole derivatives, intermediates for their preparation, pharmaceutical compositions containing therm, and to their medicinal use. The active compounds of the present invention are useful in treating migraine and other disorders.

U.S. Pat. Nos. 4,839,377 and 4,855,314 and European Patent Application Publication Number 313397 refer to 5-substituted 3-aminoalkyl indoles. The compounds are said to be useful for the treatment of migraine.

British Patent Application 040279 refers to 3-aminoalkyl-1H-indole-5-thioamides and carboxamides. The compounds are said to be useful in treating hypertension, Raymond's disease and migraine.

European Patent Application Publication Number 303506 refers to 3-poly:hydropyridyl-5-substituted-1 H-indoles. The compounds are said to have 5-$HT_1$ receptor agonist and vasoconstrictor activity and to be useful in treating migraine.

European Patent Application Publication Number 354777 refers to N-piperidinyl:indolyl:ethyl-alkane sulfonamide derivatives. The compounds are said to have 5-$HT_1$ receptor agonist and vasoconstrictor activity and to be useful in treating cephalic pain.

European Patent Application Publication Number 438230 refers to indole-substituted five-membered heteroaromatic compounds. The compounds are said to have 5-$HT_1$-like receptor agonist activity and to be useful in the treatment of migraine and other disorders for which a selective agonist of these receptors is indicated.

European Patent Application Publication Number 313397 refers to 5-heterocyclic indole derivatives. The compounds are said to have exceptional propertes for the treatment and prophylaxis of migraine, cluster headache, and headache associated with vascular disorders. These compound are also said to have exceptional "5-$HT_1$-like" receptor agonism.

International Patent Application WO 91/18897 refers to 5-heterocyclic indole derivatives. The compounds are said to have exceptional properties for the treatment and prophylaxis of migraine, cluster headache, and headache associated with vascular disorders. These compound are also said to have exceptional "5-$HT_1$-like" receptor agonism. European Patent Application Publication Number 457701 refers to aryloxy amine rivatives as having high affinity for 5$HT_{1D}$ serotonin receptors. These compounds are said to be useful for treating diseases related to serotonin receptor dysfunction, for example, migraine.

European Patent Application Publication Number 497512 A2 refers to a class of imidazole, triazole, and tetrazole derivatives which are selective agonists for 5-$HT_{1-like}$receptors. These compounds are said to be useful for treating migraine and associated disorders.

"New Trends in Benzodiazepine Research" in *Drugs of Today*, Vol. 24, 649–663 (1987) discusses the use of benzodiazepine receptor ligands in the treatment of anxiety and other disorders.

European Patent Application EP-499527-A1 refers to novel β-carboline derivatives with affinity for benzodiazepine receptors as useful in the treatment of degenerative central nervous system disorders, e.g. Alzheimer's disease.

SUMMARY OF THE INVENTION

The present invention relates to compounds of the formula

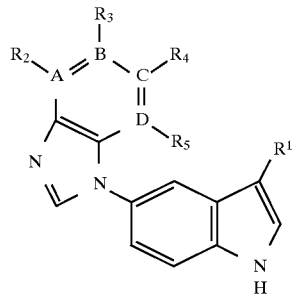

wherein $R_1$ is

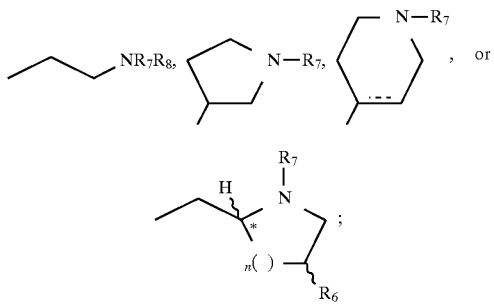

n is 0, 1, or 2; A, B, C, and D are each independently nitrogen or carbon; $R_2$, $R_3$, $R_4$, and $R_5$ are each independently hydrogen, $C_1$ to $C_6$ alkyl, aryl, $C_1$ to $C_3$ alkyl-aryl, halogen (e.g. fluorine, chlorine, bromine or iodine), cyano, nitro, —$(CH_2)_m NR_{14}R_{15}$, —$(CH_2)_m OR_9$, —$SR_9$, —$SO_2NR_{14}R_{15}$, —$(CH_2)_m NR_{14}SO_2R_{15}$, —$(CH_2)_m NR_{14}CO_2R_9$, —$(CH_2)_m NR_{14}COR_9$, —$(CH_2)_m NR_{14}CONHR_9$, —$CONR_{14}R_{15}$, or —$CO_2R_9$; $R_2$ and $R_3$, $R_3$ and $R_4$, or $R_4$ and $R_5$ may be taken together to form a five- to seven-membered alkyl ring, a six-membered aryl ring, a five- to seven-membered heteroalkyl ring having 1 heteroatom of N, O, or S, or a five- to six-membered heteroaryl ring having 1 or 2 heteroatoms of N, O, or S; $R_6$ is hydrogen, —$OR_{10}$, or —$NHCOR_{10}$; $R_7$, $R_8$, $R_{14}$, and $R_{15}$ are each independently hydrogen, $C_1$ to $C_6$ alkyl, —$(CH_2)_x OR_{11}$, $C_1$ to $C_3$ alkyl-aryl, aryl; $R_7$ and $R_8$ or $R_{14}$ and $R_{15}$ may be taken together to form a three- to six-membered ring; $R_9$ is hydrogen, $C_1$ to $C_6$ alkyl, $C_1$ to $C_3$ alkyl-aryl, or aryl; $R_{10}$ is hydrogen, $C_1$ to $C_6$ alkyl, or $C_1$ to $C_3$ alkyl-aryl; $R_{11}$ is hydrogen, $C_1$ to $C_6$ alkyl, or $C_1$ to $C_3$ alkyl-aryl; m is 0, 1, 2, or 3; x is 2 or 3; a broken line represents an optional double bond; and the above aryl groups and the aryl moieties of the above alkyl-aryl groups are independently phenyl or substituted phenyl, wherein said substituted phenyl may be substituted with one to three of $C_1$ to $C_4$ alkyl, halogen (e.g. fluorine, chlorine bromine or iodine), hydroxy, cyano, carboxamido, nitro, or $C_1$ to $C_4$ alkoxy; and the pharmaceutically acceptable salts thereof. These compounds are potent 5-$HT_1$ receptor agonists and benzodiazepine receptor agonists and antagonists and are useful in treating migraine and other disorders.

The compounds of the invention include all optical isomers of formula I (e.g. R and S stereogenicity at any chiral site) and their racemic, diastereomeric, or epimeric mixtures. When $R_6$ is equal to hydrogen, the epimers with the R absolute configuration at the chiral carbon site designated by an asterisk in formula I are preferred. When $R_6$ is equal to —OR₁₀ or —NHCOR₁₀, and n is equal to 0 or 1, the epimers with the S absolute configuration at the chiral carbon site designated by an asterisk in formula I are preferred. When R₆ is equal to —OR₁₀ or —NHCOR₁₀, and n is equal to 2, the epimers with the R absolute configuration at the chiral carbon site designated by an asterisk in formula I are preferred. When R₆ is equal to —OR₁₀ or —NHCOR₁₀, and n is equal to 0, the cis epimers [(2S, 3S) absolute configuration in the azetidine ring] are particularly preferred. When R₆ is equal to —OR₁₀ or —NHCOR₁₀, and n is equal to 1, the cis epimers [(2S, 4R) absolute configuration in the pyrrolidine ring] are particularly preferred. When R₆ is equal to —OR₁₀ or —NHCOR₁₀, and n is equal to 2, the cis epimers [(2R, 5R) absolute configuration in the piperidine ring] are particularly preferred.

Unless otherwise indicated, the alkyl and alkenyl groups referred to herein, as well as the alkyl moieties of other groups referred to herein (e.g. alkoxy), may be linear or branched, and they may also be cyclic (e.g. cyclopropyl, cyclobutyl, cyclopentyl, or cyclohexyl) or be linear or branched and contain cyclic moieties.

Preferred compounds of the invention are compounds of the formula I wherein R₁ is

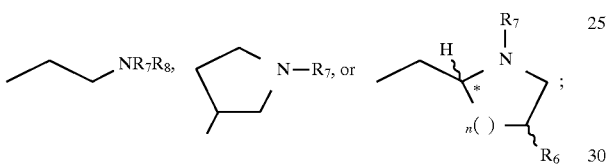

n is 1; A, B, and C are each carbon; R₆ is hydrogen or —OCH₃; R₇ is hydrogen, C₁–C₃ alkyl, or —CH₂CH₂OCH₃. Of the foregoing compounds, the R enantiomers with the chiral carbon designated by * in formula I are more preferred. Of the foregoing compounds, the cis epimers are particularly preferred.

The following compounds are particularly preferred:
5-cyano-1-[3-(N-(2-methoxyethyl)pyrrolidin-2R-ylmethyl)indol-5-yl]-1H-benzimidazole;
5-methoxycarbonyl-1-[3-(N-(2-methoxyethyl)pyrrolidin-2R-ylmethyl)indol-5-yl]-1H-benzimidazole;
5-cyano-1-[3-(4R-methoxypyrrolidin-2R-ylmethyl)indol-5-yl]-1H-benzimidazole;
5-cyano-1-[3-(N-(2-methoxyethyl)-4R-methoxypyrrolidin-2R-ylmethyl)indol-5-yl]-1H-benzimidazole;
5-hydroxymethyl-1-[3-(N-(2-methoxyethyl)pyrrolidin-2R-ylmethyl)indol-5-yl]-1H-benzimidazole;
5-cyano-1-[3-(pyrrolidin-2R-ylmethyl)indol-5-yl]-1H-benzimidazole;
1-[3-(N-cyclopropylmethly)pyrrolidin-2R-ylmethyl)indol-5-yl]-3H-imidazo[4,5-b]pyridine;
1-[3-(pyrrolidin-2R-ylmethyl)indol-5-yl]-3H-imidazo[4,5-b]pyridine;
5-cyano-1-[3-(N-methylpyrrolidin-2R-ylmethyl)indol-5-yl]-1H-benzimidazole;
5-cyano-1-[3-(N-cyclopropylmethyl)pyrrolidin-2R-ylmethyl)indol-5-yl]-1H-benzimidazole;
1-[3-(N-methylpyrrolidin-2R-ylmethyl)indol-5-yl]-1H-benzimidazole;
5-methyl-1-[3-(N-methylpyrrolidin-2R-ylmethyl)indol-5-yl]-1H-benzimidazole;
1-[3-(N-methylpyrrolidin-2R-ylmethyl)indol-5-yl]-3H-imidazo[4,5-b]pyridine;
6-methoxy-1-[3-(N-methylpyrrolidin-2R-ylmethyl)indol-5-yl]-3H-imidazo[4,5-b]pyridine;
1-[3-(N-methylpyrrolidin-2R-ylmethyl)indol-5-yl]-5-trifluoromethyl-1H-benzimidazole;
1-[3-(2-N,N-dimethylaminoethyl)indol-5-yl]-3H-imidazo[4,5-b]pyridine;
1-[3-(2-aminoethyl)indol-5-yl]-3H-imidazo[4,5-b]pyridine;
1-[3-(N-methylpyrrolidin-2R-ylmethyl)indol-5-yl]-5-phenyl-1H-benzimidazole;
6,7-dichloro-1-[3-(N-methylpyrrolidin-2R-ylmethyl)indol-5-yl]-1H-benzimidazole;
1-[3-(piperid-4-yl)indol-5-yl]-3H-imidazo[4,5-b]pyridine;
1-[3-(N-methylpyrrolidin-3-yl)indol-5-yl]-3H-imidazo[4,5-b]pyridine;
5-chloro-1-[3-(N-methylpyrrolidin-2R-ylmethyl)indol-5-yl]-1H-benzimidazole;
6-chloro-1-[3-(N-methylpyrrolidin-2R-ylmethyl)indol-5-yl]-1H-benzimidazole;
7-chloro-1-[3-(N-methylpyrrolidin-2R-ylmethyl)indol-5-yl]-1H-benzimidazole;
5-aminomethyl-1-[3-(N-(2-methoxyethyl)pyrrolidin-2R-ylmethyl)indol-5-yl]-1H-benzimidazole;
5-acetylaminomethyl-1-[3-(N-(2-methoxyethyl)pyrrolidin-2R-ylmethyl)indol-5yl]-1H-benzimidazol;
5-cyano-1-[3-(piperid-4yl)indol-5-yl]-1H-benzimidazole;
5-cyano-1-[3-(1,2,5,6-tetrahydropyrid-4-yl)indol-5-yl]-1H-benzimidazole;
N-phenyl-N'-[3-(N-(2-methoxyethyl)pyrrolidin-2R-ylmethyl)indol-5-yl]-1H-benz[b]imidazyl]methylurea;
5-cyano-1-[3-(N-methylpyrrolidin-3-yl)indol-5-yl]-1H-benzimidazole;
5-benzylaminoethyl-1-[3-(N-(2-methoxyethyl)pyrrolidin-2R-ylmethyl)indol-5-yl]-1H-benzimidazol;
5-aminomethyl-1-[3-N-methylpyrrolidin-2R-ylmethyl)indol-5yl]-1H-benzimidazole;
5-cyano-1-[3-(N-methylpyrrolidin-2R-ylmethyl)indol-5-yl]-1H-pyrido[4,5-b]imidazole; and
4-methyl-1-[3-(N-methylpyrrolidin-2R-ylmethyl)indol-5-yl]-1H-pyrido[4,5-b]midazole.

The present invention also relates to a compound of the formula

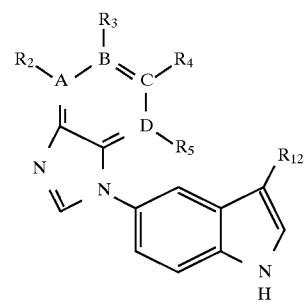

wherein R₁₂ is

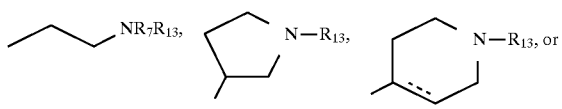

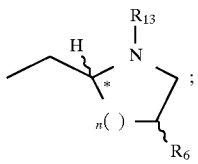

n is 0, 1, or 2; A, B, C, and D are each independently nitrogen or carbon; $R_2$, $R_3$, $R_4$, and $R_5$ are each independently hydrogen, $C_1$ to $C_6$ alkyl, aryl, $C_1$ to $C_3$ alkyl-aryl, halogen (e.g. fluorine, chlorine, bromine or iodine), cyano, nitro, $-(CH_2)_m NR_{14}R_{15}$, $-(CH_2)_m OR_9$, $-SR_9$, $-SO_2NR_{14}R_{15}$, $-(CH_2)_m NR_{14}SO_2R_{15}$, $-(CH_2)_m NR_{14}CO_2R_9$, $-(CH_2)_m NR_{14}COR_9$, $-(CH_2)_m NR_{14}CONHR_9$, $-CONR_{14}R_{15}$, or $-CO_2R_9$; $R_2$ and $R_3$, $R_3$ and $R_4$, or $R_4$ and $R_5$ may be taken together to form a five- to seven-membered alkyl ring, a six-membered aryl ring, a five- to seven-membered heteroalkyl ring having 1 heteroatom of N, O, or S, or a five to six-membered heteroaryl ring having 1 or 2 heteroatoms of N, O, or S; $R_6$ is hydrogen, $-OR_{10}$, or $-NHCOR_{10}$; $R_7$, $R_{14}$, and $R_{15}$ are each independently hydrogen, $C_1$ to $C_6$ alkyl, $-(CH_2)_x OR_{11}$, $C_1$ to $C_3$ alkyl-aryl, or aryl; $R_{14}$ and $R_{15}$ may be taken together to form a three- to six-membered ring; $R_9$ is hydrogen, $C_1$ to $C_6$ alkyl, $C_1$ to $C_3$ alkyl-aryl, or aryl; $R_{10}$ is hydrogen, $C_1$ to $C_6$ alkyl, or $C_1$ to $C_3$ alkyl-aryl; $R_{11}$ is hydrogen, $C_1$ to $C_6$ alkyl, or $C_1$ to $C_3$ alkyl-aryl; $R_{13}$ is $-COR_{16}$, $-CO_2R_{16}$, or $-CH_2Ph$; $R_{16}$ is $C_1$ to $C_1$ alkyl, $C_1$ to $C_3$ alkyl-aryl, or aryl; m is 0, 1, 2, or 3; x is 2 or 3; a broken line represents an optional double bond; and the above aryl groups and the aryl moieties of the above alkyl-aryl groups are independently phenyl and substituted phenyl, wherein said substituted phenyl may be substituted with one to three of $C_1$ to $C_4$ alkyl, halogen (e.g. fluorine, chlorine bromine or iodine), hydroxy, cyano, carboxamido, nitro, and $C_1$ to $C_4$ alkoxy. These compounds are useful as intermediates in preparing compounds of formula I.

The present invention also relates to a pharmaceutical composition for treating a condition selected from hypertension, depression, anxiety, eating disorders, obesity, drug abuse, cluster headache, migraine, pain, and chronic paroxysmal hemicrania and headache associated with vascular disorders comprising an amount of a compound of the formula I or a pharmaceutically acceptable salt thereof effective in treating such condition and a pharmaceutically acceptable carrier.

The present invention also relates to a method for treating a condition selected from hypertension, depression, anxiety, eating disorders, obesity, drug abuse, cluster headache, migraine, pain and chronic paroxysmal hemicrania and headache associated with vascular disorders comprising administering to a mammal (e.g., a human) requiring such treatment an amount of a compound of the formula I or a pharmaceutically acceptable salt thereof effective in treating such condition.

The present invention also relates to a method for treating disorders arising from deficient serotonergic neurotransmission (e.g., depression, anxiety, eating disorders, obesity, drug abuse, cluster headache, migraine, pain and chronic paroxysmal hemicrania and headache associated with vascular disorders) comprising administering to a mammal (e.g., a human) requiring such treatment an amount of a compound of the formula I or a pharmaceutically acceptable salt thereof effective in treating such condition.

DETAILED DESCRIPTION OF THE INVENTION

The compounds of formula I can be prepared via the following reaction scheme:

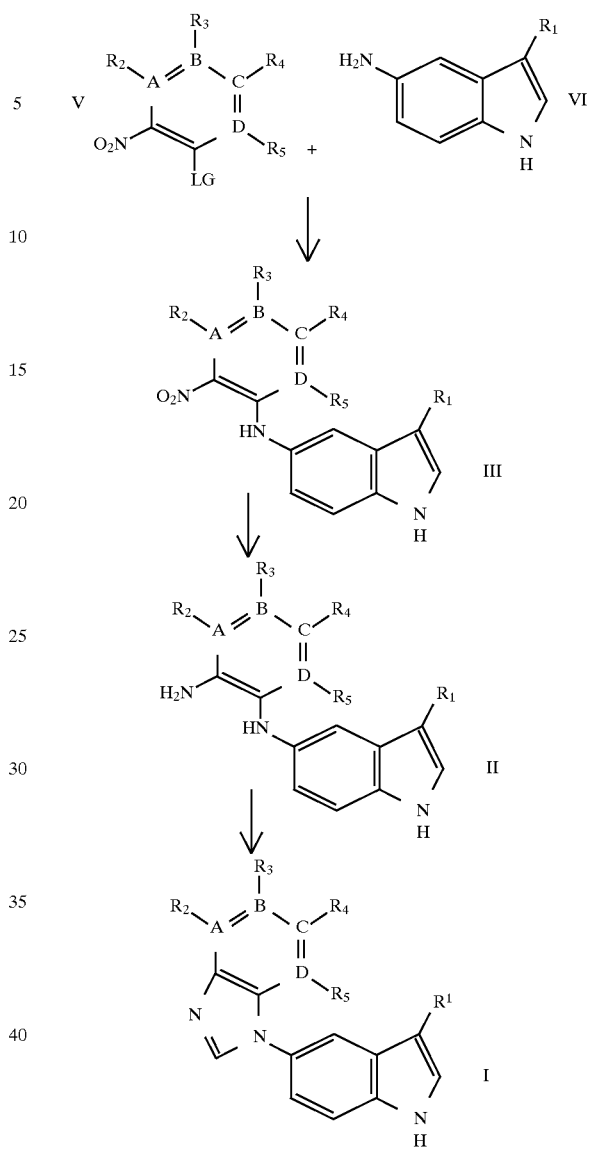

Compounds of formula III can be prepared by reacting a compound of formula VI wherein $R_1$ is as defined for formula I with a compound of formula V wherein A, B, C, D, $R_2$, $R_3$, $R_4$, and $R_5$ are as defined for formula I and where LG is a suitable leaving group such as, for example, F, Cl, Br, I, $-SCH_3$, $-SO_2CH_3$, $-SPh$, or $-SO_2Ph$ (Ph=phenyl), under acidic, neutral, or basic conditions in an inert solvent. Basic conditions are preferred. Suitable bases include sodium hydrogen carbonate, sodium carbonate, trialkylamines (including, for example, triethylamine), sodium, and sodium hydride. Triethylamine is the preferred base. Suitable solvents includes $C_1$ to $C_4$ alcohols, dioxane, diethyl ether, tetrahydrofuran, acetonitrile, N,N-dimethylformamide, and N-methylpyrrolidine. Ethanol is the preferred solvent. The reaction is usually conducted at a temperature of from about 25° C. to about 154° C., preferably from about 70° C. to about 80° C.

Compounds of formula II can be prepared from a reduction of compounds of formula III wherein A, B, C, D, $R_1$, $R_2$, $R_3$, $R_4$, and $R_5$ are as defined for formula I in an inert solvent. This reduction can be mediated either by transition metals or other metal reducing agents. When a transition metal mediates the reduction, a hydrogen source is also used. Suitable transition metals include palladium on carbon, palladium hydroxide on carbon, and platinum oxide. Palladium on carbon is preferred. Suitable hydrogen sources include hydrogen gas, ammonium formate, and formic acid. Hydrogen gas at a pressure of from about one to about three atmospheres is the preferred hydrogen source. Three atmospheres of hydrogen gas is the preferred pressure. Suitable solvents include $C_1$ to $C_4$ alcohols, acetonitrile, N,N-dimethylformamide, and N-methylpyrrolidine. Ethanol is the preferred solvent. Other metal reducing agents include $FeSO_4$, Zn (metal) in aqueous hydrochloric acid, and Sn (metal) in aqueous hydrochloric acid. Of this group $FeSO_4$ is preferred. Suitable solvents include aqueous ammonium hydroxide (mixed with ethanol) or concentrated aqueous hydrochloric acid. Aqueous ammonium hydroxide (mixed with ethanol) is the preferred solvent. All of the above reduction reactions are usually conducted at a temperature of from about 25° C. to about 100° C., preferably from about 25° C. to about 50° C. It should be noted that compounds of formula II are used directly from the reduction reaction with no purification.

Compounds of formula I are prepared from the reaction of a compound of formula II wherein A, B, C, D, $R_1$, $R_2$, $R_3$, $R_4$, and $R_5$ are as defined for formula I with a formic acid synthon under neutral or acidic conditions in an inert solvent. Suitable formic acid synthons include dimethylformamide dimethylacetal, trimethyl orthoformate, triethyl orthoformate, ethoxymethylenemalononitrile, and diethyl ethoxymethylene malonate. Ethoxymethylenemalononitrile is the preferred formic acid synthon. Neutral conditions are preferred using ethoxymethylenemalononitrile. Suitable acid catalysts which can be used with the above formic acid synthons include p-toluenesulfonic acid, hydrochloric acid, formic acid, or acidic acid. Suitable solvents include $C_1$ to $C_4$ alcohols, dioxane, diethyl ether, tetrahydrofuran, acetonitrile, N,N-dimethylformamide, and N-methylpyrrolidine. 2-Propanol is the preferred solvent. The reaction is usually conducted at a temperature of from about 25° C. to about 154° C., preferably from about 75° C. to about 85° C.

Compounds of formula I can also be prepared via an alternate route shown in the scheme below:

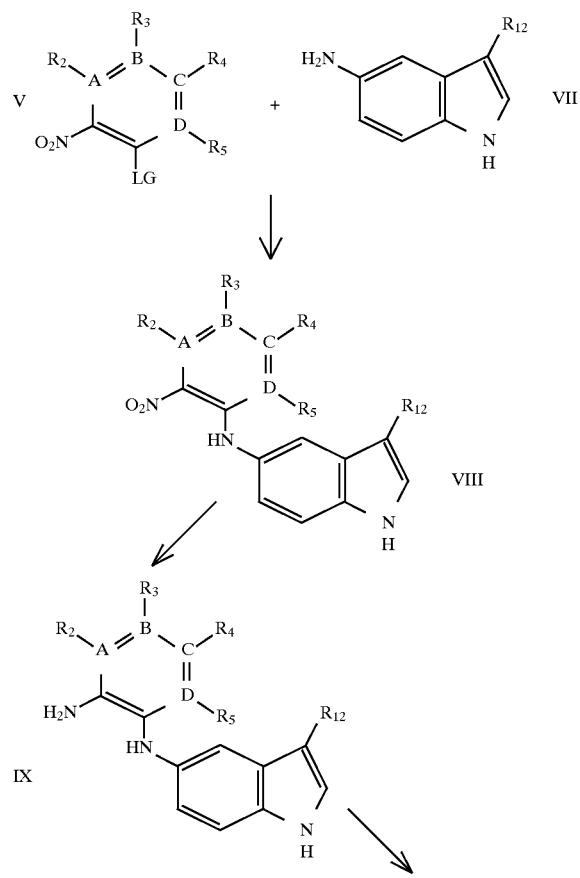

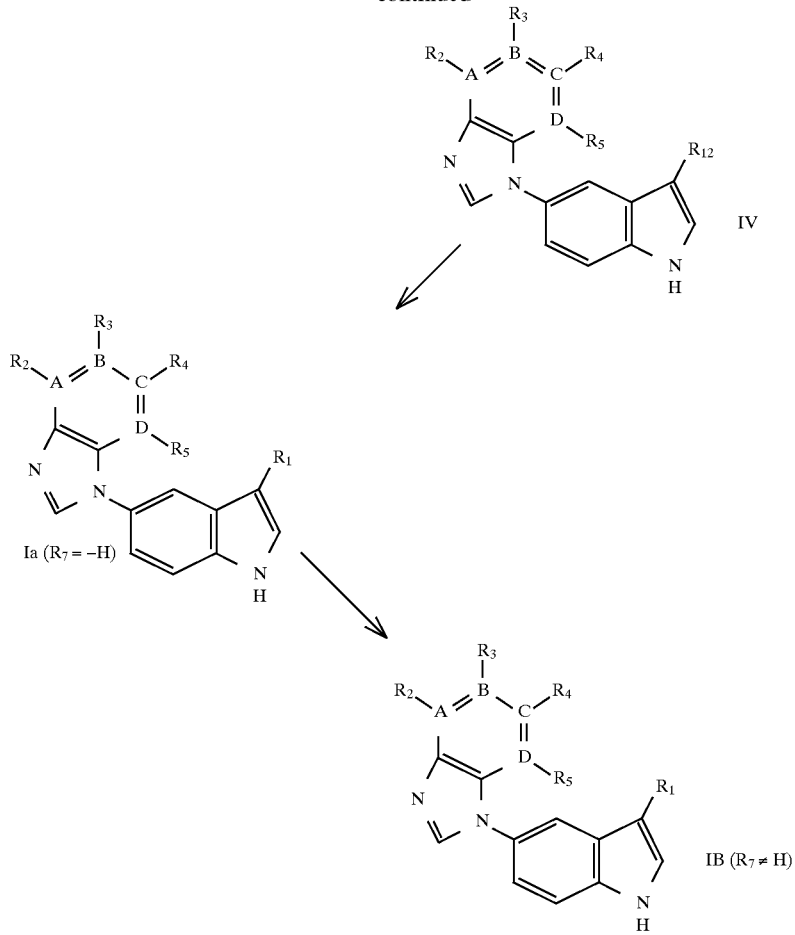

Compounds of formula VIII can be prepared by reacting a compound of formula VII wherein $R_{12}$ is as defined for formula IV with a compound of formula V wherein A, B, C, D, $R_2$, $R_3$, $R_4$, and $R_5$ are as defined for formula I and where LG is a suitable leaving group such as, for example, F, Cl, Br, I, —$SCH_3$, —$SO_2CH_3$, —SPh, or —$SO_2Ph$, under acidic, neutral, or basic conditions in an inert solvent. Basic conditions are preferred. Suitable bases include sodium hydrogen carbonate, sodium carbonate, trialkylamines (including, for example, triethylamine), sodium, and sodium hydride. Triethylamine is the preferred base. Suitable solvents includes $C_1$ to $C_4$ alcohols, dioxane, diethyl ether, tetrahydrofuran, acetonitrile, N,N-dimethylformamide, and N-methylpyrrolidine. Ethanol is the preferred solvent. The reaction is usually conducted at a temperature of from about 25° C. to about 154° C., preferably about 70° C. to about 80° C.

Compounds of formula IX can be prepared from a reduction of compounds of formula VIII wherein A, B, C, D, $R_2$, $R_3$, $R_4$, R5, and $R_{12}$ are as defined for formula IV in an inert solvent. This reduction can be mediated either by transition metals or other metal reducing agents. When a transition metal mediates the reduction, a hydrogen source is also used. Suitable transition metals include palladium on carbon, palladium hydroxide on carbon, and platinum oxide. Palladium on carbon is preferred. Suitable hydrogen sources include hydrogen gas, ammonium formate, and formic acid. Hydrogen gas at a pressure of about one to about three atmospheres is the preferred hydrogen source. Three atmospheres of hydrogen gas is the preferred pressure. Suitable solvents include $C_1$ to $C_4$ alcohols, acetonitrile, N,N-dimethylformamide, and N-methylpyrrolidine. Ethanol is the preferred solvent. Other metal reducing agents include $FeSO_4$, Zn (metal) in aqueous hydrochloric acid, and Sn (metal) in aqueous hydrochloric acid. Of this group $FeSO_4$ is preferred. Suitable solvents include aqueous ammonium hydroxide (mixed with ethanol) or concentrated aqueous hydrochloric acid. Aqueous ammonium hydroxide (mixed with ethanol) is the preferred solvent. All of the above reduction reactions are usually conducted at a temperature of from about 25° C. to about 100° C., preferably about 25° C. to about 50° C. It should be noted that compounds of formula IX are used directly from the reduction reaction with no purification.

Compounds of formula IV are prepared from the reaction of a compound of formula IX wherein A, B, C, D, $R_2$, $R_3$, $R_4$, $R_5$, and $R_{12}$ are as defined for formula IV with a formic acid synthon under neutral or acidic conditions in an inert solvent. Suitable formic acid synthons include dimethylformamide dimethylacetal, trimethyl orthoformate, triethyl orthoformate, ethoxymethylenemalononitrile, and diethyl ethoxymethylene malonate. Ethoxymethylenemalononitrile is the preferred formic acid synthon. While neutral conditions are preferred, suitable acid catalysts include p-toluenesulfonic acid, hydrochloric acid, formic acid, or acidic acid. Suitable solvents include $C_1$ to $C_4$ alcohols, dioxane, diethyl ether, tetrahydrofuran, acetonitrile, N,N-dimethylformamide, and N-methylpyrrolidine. 2-Propanol is the preferred solvent. The reaction is usually conducted at a temperature of from about 25° C. to about 154° C., preferably about 75° C. to about 85° C.

Compounds of formula IA wherein $R_7$ is hydrogen can be prepared by the deprotection of the basic nitrogen in compounds of formula IV where A, B, C, D, $R_2$, $R_3$, $R_4$, $R_5$, and $R_{12}$ are as defined for formula IV in an inert solvent. The nature of this deprotection is dependent on the nature of $R_{13}$. When $R_{13}$ is —$CH_2Ph$ or —$CO_2CH_2Ph$, this deprotection can be performed via a catalytic hydrogenation using a hydrogen source and a transition metal catalyst in an inert solvent. Suitable transition metals include palladium on carbon, palladium hydroxide on carbon, and platinum oxide. Palladium on carbon is preferred. Suitable hydrogen sources include hydrogen gas, ammonium formate, and formic acid. Hydrogen gas at a pressure of about one to about three atmospheres is the preferred hydrogen source. Three atmospheres of hydrogen gas is the preferred pressure. Suitable solvents include $C_1$ to $C_4$ alcohols, acetonitrile, N,N-dimethylformamide, and N-methylpyrrolidine. Ethanol is the preferred solvent. The reaction is usually conducted at a temperature of from about 25° C. to about 100° C., preferably about 25° C. to about 50° C. When $R_{13}$ is —$COR_{16}$, or —$CO_2R_{16}$ wherein $R_{16}$ is as defined for formula IV, deprotection can be accomplished by basic or acidic hydrolysis. Suitable bases include sodium hydroxide, sodium alkoxides, and potassium t-butoxide. Suitable acids in mineral acids and sulfuric acid. Suitable solvents include water and $C_1$ to $C_3$ alcohols. The reaction is usually conducted at a temperature of from about 25° C. to about 100° C., preferably about 70° C. to about 80° C.

Compounds of formula IB wherein $R_7$ is not hydrogen can be prepared via alkylation of a compound of formula IA wherein $R_7$ is hydrogen and A, B, C, D, $R_1$, $R_2$, $R_3$, $R_4$, and $R_5$ are as defined for formula I with an alkylating agent of the formula $R_7$-G where G is a suitable leaving group and a base in an inert solvent. Suitable alkylating agents include alkyl halides (chlorides, bromides, or iodides), alkyl tosylates, alkyl mesylates, alkyl triflates, α,β-unsaturated ketones, α,β-unsaturated esters, α,β-unsaturated aldehydes, α,β-unsaturated amides, and α,β-unsaturated nitriles. Alkyl halides (iodides) are preferred. Suitable bases include sodium hydrogen carbonate, sodium carbonate, trialkylamines (including, for example, triethylamine), sodium, and sodium hydride. Triethylamine is the preferred base. Suitable solvents include methylene chloride, chloroform, carbon tetrachloride, acetonitrile, tetrahydrofuran, diethyl ether, dioxane, N,N-dimethylformamide, ethanol, propanol, methanol. The preferred solvent is acetonitrile. The reaction is conducted between a temperature of about 0° C. to about 150° C., preferably from about 25° C. to about 65° C.

Compounds of formula I wherein $R_3$ is —$CH_2NH_2$ can be prepared via the reduction of a compound of formula I wherein $R_3$ is —CN in an inert solvent. Suitable reducing conditions include lithium aluminum hydride and Raney nickel in conjunction with hydrogen. The preferred reducing conditions are Raney nickel in conjunction with hydrogen, preferably at a pressure of approximately three atmospheres of hydrogen. Suitable inert solvent include diethyl ether, tetrahydrofuran, $C_1$ to $C_3$ alcohols, and N,N-dimethylformamide. The preferred solvent is ethanol. The reaction is conducted between a temperature of about 0° C. to about 100 ° C., preferably at about 25° C.

Compounds of formula I wherein $R_3$ is —$CH_2NH(C=O)R_9$ and $R_9$ is as defined for formula I can be prepared via the acylation of a compound of formula I wherein $R_3$ is —$CH_2NH_2$ with an active ester derivative of a carboxylic acid of the formula $R_9CO_2H$ wherein $R_9$ is as defined above in an inert solvent usually in the presence of a base. Suitable active esters derivatives include acid chlorides, imidazylcarboxamides, anhydrides, and p-nitrophenyl esters. The preferred active esters derivative are acid chlorides. Suitable bases include trialkylamines, sodium carbonate, and sodium bicarbonate. The preferred base is triethylamine. Suitable inert solvents include diethyl ether, tetrahydrofuran, 1,4-dioxane, methylene chloride, 1,2-dichloroethane, $C_1$ to $C_3$ alcohols, and N,N-dimethylformamide. The preferred inert solvent is ethanol. The reaction is conducted between a temperature of about 0° C. to about 100° C., preferably at about 25° C.

Compounds of formula I wherein $R_3$ is —$CH_2NH(C=O)NHR_9$ and $R_9$ is as defined for formula I can be prepared via the reaction of a compound of formula I wherein $R_3$ is —$CH_2NH_2$ with an isocyanate of the formula O=C=$NR_9$ wherein $R_9$ is as defined above in an inert solvent usually in the presence of a base. Suitable bases include trialkylamines, sodium carbonate, and sodium bicarbonate. The preferred base is triethylamine. Suitable inert solvents include diethyl ether, tetrahydrofuran, 1,4-dioxane, methylene chloride, 1,2-dichloroethane, $C_1$ to $C_3$ alcohols, and N,N-dimethylformamide. The preferred inert solvent is ethanol. The reaction is conducted between a temperature of about 0° C. to about 100° C., preferably at about 25° C.

Compounds of formula V are either commercially available or available by methods known to one skilled in the art.

Compounds of formula VI and formula VII can be prepared as shown in the following reaction scheme:

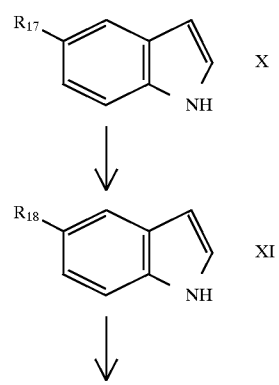

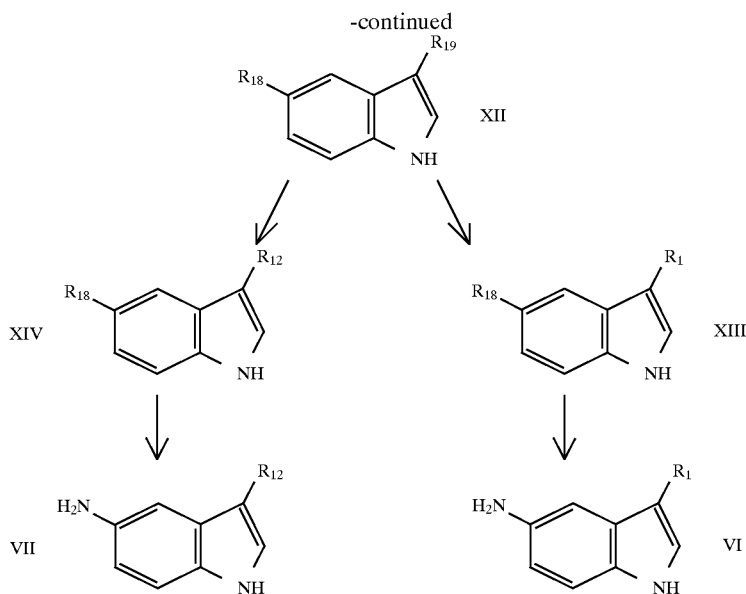

Compounds of formula XI wherein $R_{18}$ is —$N(R_{20})_2$-NHCOR$_{20}$, or 2,5-dimethyl-1H-pyrrole and $R_{20}$ is benzyl or substituted benzyl are prepared via the alkylation or acylation of a compound of formula X wherein $R_{17}$ is —NH$_2$ with benzyl or substituted benzyl halides (preferable benzyl bromide), benzoyl or substituted benzoyl halides (preferably benzoylchloride) in the presence of a base in an inert solvent, or via condensation with 1,4dicarbonyl compounds under dehydrative conditions in an inert solvent. For the alkylation reaction, suitable bases include sodium bicarbonate, sodium carbonate, sodium hydride, and trialkylamines. Triethylamine is the preferred base. Suitable solvents include dimethylformamide, ethers (including tetrahydrofuran), and $C_1$–$C_3$ alcohols. Tetrahydrofuran is the preferred solvent. The reaction is usually conducted at a temperature of from about 25° C. to about 100° C., preferably at about 25° C. For the dehydrative condensation, acetonoylacetone is the preferred 1,4-dicarbonyl compound. Suitable solvents include benzene, toluene, and xylenes. Toluene is the preferred solvent. Dehydration can be accomplished using molecular sieves, drying agents, or a Dean-Stark trap. The Dean-Stark trap is preferred. The reaction is usually conducted at a temperature of from about 70° C. to about 150° C., preferably from about 70° C. to about 80° C.

Compounds of formula XII wherein $R_{19}$ is

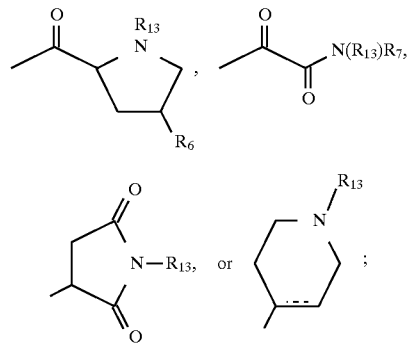

$R_6$ and $R_7$ are as defined for formula I and $R_{13}$ is as defined for formula IV can be prepared by reaction of a compound of formula XI wherein $R_{18}$ is —$N(R_{20})_2$, —NHCOR$_{20}$, or 2,5-dimethyl-1H-pyrrole and $R_{20}$ is benzyl or substituted benzyl with a suitable electrophile under acidic, basic, or neutral conditions. Suitable electrophiles include N-protected proline acid chlorides, N-protected4-piperidones, oxalyl chloride, or maleimides. In the case of oxalyl chloride, the resulting indole-3-glyoxamic acid chloride is further reacted with a secondary amine of the formula HNR$_7$R$_8$ where $R_7$ and $R_8$ are as defined for formula I. Suitable acids include mineral acids, acetic acid, or formic acid. Suitable bases include Grignard reagents including ethyl magnesium bromide, primary, secondary or tertiary amines, sodium or potassium metal, or sodium hydride. Suitable solvents include ethers (including tetrahydrofuran and diethylether), benzene, toluene, acetic acid, formic acid, or $C_1$–$C_4$ alcohols. The reaction is usually conducted at a temperature from about 0° C. to 150° C., preferably in the range of from about 0° C. to about 120° C. For example, in the case where the electrophile is an N-protected proline acid chloride, the preferred solvent is benzene, the reaction is preferably run under basic conditions using ethyl magnesium bromide as the preferred base, and the reaction is run at a temperature preferably about 0° C.; in the case where the electrophile is an N-protected4-piperidone, the preferred solvent is methanol, the reaction is preferably run under basic conditions using sodium methoxide as the preferred base, and the reaction is run at a temperature preferably about 65° C.; in the case where the electrophile is oxalyl chloride, the preferred solvent is ether, the reaction is preferably run under basic conditions using HNR$_7$R$_8$ as the preferred base, and the reaction is run at a temperature preferably about 0° C.; and in the case where the electrophile is a maleimide, the preferred solvent is acetic acid, the reaction is preferably run under acidic conditions using acetic acid as the preferred acid, and the reaction is run at a temperature preferably about 101° C.

Compounds of formula XIII wherein R, is as defined in formula I and formula XIV defined wherein $R_{12}$ is as defined for formula IV can be prepared via reduction of a compound of formula XII wherein $R_{19}$ is

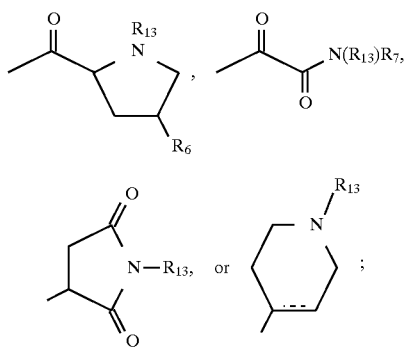

$R_6$ and $R_7$ are as defined for formula I, $R_{13}$ is as defined for formula IV, and $R_{18}$ is as defined for formula XI in an inert solvent. Suitable reducing agents include lithium aluminum hydride, lithium borohydride, and diborane. Lithium aluminum hydride is preferred for the formation of compounds of formula XIII. Lithium borohydride is preferred for the formation of compounds of formula XIV. Suitable inert solvents include tetrahydrofuran, dioxane, and other ethers. Tetrahydrofuran is the preferred solvent. The reaction is usually conducted at a temperature of from about 25° C. to about 100° C., preferably at about 65° C.

Compounds of formula VII wherein $R_{12}$ is as defined for formula IV can be prepared via the deprotection of the C5-indole nitrogen of a compound of formula XIV wherein $R_{12}$ is as defined for formula IV and $R_{18}$ is as defined for formula XI using a transition metal catalyst and a hydrogen source or hydroxylamine hemihydrochloride. Suitable solvents include $C_1$–$C_4$ alcohols, ethyl acetate, acetone, and dimethylformamide. Ethanol is the preferred solvent. Suitable transition metal catalysts include palladium on carbon, palladium hydroxide on carbon, and platinum oxide. The preferred catalyst is palladium hydroxide on carbon. Suitable hydrogen sources include hydrogen gas, ammonium formate, and formic acid. Hydrogen gas is preferred, usually at a pressure of from about 1 to about 3 atmospheres, preferably at 3 atmospheres pressure. The reaction is usually conducted at a temperature of from about 25° C. to about 100° C., preferably at about 40° C. When hydroxylamine hemihydrochloride is used to deprotect the indole nitrogen, ethanol is the preferred solvent, and the preferred reaction temperature is from about 70° C. to about 80° C.

Compounds of formula VI can be prepared via the deprotection of the C5-indole nitrogen of a compound of formula XIII where $R_1$ is as defined for formula I and $R_{18}$ is as defined for formula XI using a transition metal catalyst and a hydrogen source or hydroxylamine hemihydrochloride. Suitable solvents include $C_1$–$C_4$ alcohols, ethyl acetate, acetone, and dimethylformamide. Ethanol is the preferred solvent. Suitable transition metal catalysts include palladium on carbon, palladium hydroxide on carbon, and platinum oxide. The preferred catalyst is palladium hydroxide on carbon. Suitable hydrogen sources include hydrogen gas, ammonium formate, and formic acid. Hydrogen gas is preferred, usually at a pressure of from about 1 to about 3 atmospheres, preferably at 3 atmospheres pressure. The reaction is usually conducted at a temperature of from about 25° C. to about 100° C., preferably at about 40° C. When hydroxylamine hemihydrochloride is used to deprotect the indole nitrogen, ethanol is the preferred solvent, and the preferred reaction temperature is about 70° C. to about 80° C.

Compounds of formula X where $R_{17}$ is —$NH_2$ or —$NO_2$ are either commercially available or can be prepared using methods known to one skilled in the art.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature, e.g., where $R_2$ contains a carboxylate, are capable of forming base salts with various pharmacologically acceptable cations. Examples of such salts include the alkali metal or alkaline-earth metal salts and particular, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction of maximum product of yields of the desired final product.

The compounds of the formula I and the pharmaceutically acceptable salts thereof (hereinafter, also referred to as the active compounds of the invention) are useful psychotherapeutics and are potent serotonin (5-HT$_1$) agonists and benzodiazepine agonists and antagonists, and may be used in the treatment of depression, anxiety, eating disorders, obesity, drug abuse, cluster headache, migraine, chronic paroxysmal hemicrania and headache associated with vascular disorders, pain, and other disorders arising from deficient serotonergic neurotransmission. The compounds can also be used as centrally acting antihypertensives and vasodilators. The active compounds of the invention are evaluated as antimigraine agents by testing the extent to which they mimic sumatriptan in contracting the dog isolated saphenous vein strip [P. P. A. Humphrey et al., *Br. J. Pharmacol.*, 94, 1128 (1988)]. This effect can be blocked by methiothepin, a known serotonin antagonist. Sumatriptan is known to be useful in the treatment of migraine and produces a selective increase in carotid vascular resistance in the anesthetized dog. It has been suggested [W. Fenwick et al., *Br. J. Pharmacol.*, 96, 83 (1989)] that this is the basis of its efficacy.

The active compounds of the present invention can also be evaluated via the plasma protein extravasation response within the dura mater of guinea pigs following unilateral electrical trigeminal ganglion stimulation as described in Markowitz et al., *J. Neurosci.*, 7 (12), 4129–4136 (1987). The extent to which they mimic sumatriptan, in terms of both potency and efficacy, is determined in this assay.

The serotonin 5-$HT_1$ agonist activity is measured in in vitro receptor binding assays as described for the 5-$HT_{1A}$ receptor using rat cortex as the receptor source and [$^3$H]-8-OH-DPAT as the radioligand [D. Hoyer et al. *Eur. J. Pharm.*, Vol. 118, 13 (1985)] and as described for the 5-$HT_{1D}$ receptor using bovine caudate as the receptor source and [$^3$H]serotonin as the radioligand [R. E. Heuring and S.J. Peroutka, *J. Neuroscience*, Vol.7, 894 (1987)]. Affinity for benzodiazepine receptors is measured in in vitro receptor binding assays using guinea pig cerebellum as the receptor source and [$^3$H]flunitrazepam as the radioligand [P. Supavilai and M. Karobath *Eur. J. Pharm.* Vol. 70, 183 (1981)].

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Uquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

For buccal administration the composition may take the form of tablets or lozenges formulated in conventional manner.

The active compounds of the invention may be formulated for parenteral administration by injection, including using conventional catheterization techniques or infusion. Formulations for injection may be presented in unit dosage form e.g. in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g. sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g. dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., migraine) is 0.1 to 200 mg of the active ingredient per unit dose which could be administered, for example, 1 to 4 times per day.

Aerosol formulations for treatment of the conditions referred to above (e.g., migraine) in the average adult human are preferably arranged so that each metered dose or "puff" of aerosol contains 20 μg to 1000 μg of the compound of the invention. The overall daily dose with an aerosol will be within the range 100 μg to 10 μg. Administration may be several times daily, for example 2, 3, 4 or 8 times, giving for example, 1, 2 or 3 doses each time.

The following non-limiting Examples illustrate the preparation of the compounds of the present invention. Commercial reagents were utilized without further purification. Melting points are uncorrected. NMR data are reported in parts per million (d) and are referenced to the deuterium lock signal from the sample solvent. Specific rotations were measured at room temperature using the sodium D line (589 nm). Unless otherwise stated, all mass spectrum were performed using electron impact (EI, 70 eV) conditions. Chromatography refers to column chromatography performed using 32–63 μm silica gel and executed under nitrogen pressure (flash chromatography) conditions. Room temperature refers to 20°–25° C.

EXAMPLE 1

General Synthesis of 1-Indolyl-1H-benzimidazoles and 1-Indolyl-3H-imidazo[4,5-b]pyridines A mixture of a 5-(2-nitroarylamino)-1H-indole (2.00 mmol) and Pd on carbon (20% by weight) in absolute ethanol was shaken under a hydrogen atmosphere (3 atm) at room temperature for 8 hours. The resulting reaction mixture was filtered through Celite®, and the filtrate was evaporated under reduced pressure to afford crude 5-(2-aminoarylamino)-1H-indole, which was used directly. Alternatively, a mixture of a 5-(2-nitroarylamino)-1H-indole (2.00 mmol) and $FeSO_4$ (5.5 g, 20 mmol, 10 eq) in ammonium hydroxide/water/ethanol [1:5:3, respectively, 27 mL total volume] was stirred at room temperature for 24 hours. The resulting reaction mixture was then filtered through Celite®, and ethanol was removed from the filtrate via evaporation under reduced pressure. The remaining aqueous mixture was extracted with methylene chloride (3×25 mL), and the organic extracts were combined, dried (MgSO$_4$), and evaporated under reduced pressure to afford crude 5-(2-aminoarylamino)-1H-indole, which was used directly.

Then, the 5-(2-aminoarylamino)-1H-indole and either dimethylformamide dimethylacetal (10 mL), triethyl orthoformate/formic acid (5 mL/5 mL), or ethoxymethylene-malononitrile (0.49 g, 4.01 mmol, 2.0 eq) in 2-propanol (10 mL) was heated at reflux under nitrogen for 1 to 24 hours, depending on the substrate. When dimethylformamide dimethylacetal was used, the reaction solvent is changed to toluene after 1 hour, a catalytic amount (5 mg) of p-toluenesulfonic acid was added, and the reaction solution was heated at reflux under nitrogen for 12–24 hours depending on the substrate. The resultant reaction solution was then evaporated under reduced pressure, and the residue was column chromatographed using silica gel (approximately 50 g) and an appropriate solvent system to afford the appropriate 1-indolyl-1H-benzimidazole or 1-indolyl-3H-imidazo[4,5-b]pyridine.

Following this procedure the following compounds were prepared.

A. 5-Cyano-1-[3-(N-(2-methoxyethyl)pyrrolidin-2R-ylmethyl)indol-5-yl]-1H-benzimidazole 5-(4-Cyano-2-nitrophenylamino)-3-(N-(2-methoxyethyl) pyrrolidin-2R-ylmethyl)-1H-indole was used. Reduction was by catalytic hydrogenation, the cyclization reaction used ethoxymethylenemalononitrile in propanol, and the cyclization reaction was heated for 2 hours. Chromatography using 18:1:1 [ethyl acetate/methanol/triethylamine] afforded the title compound (83%) as a white foam: $^{13}$C NMR (CD$_3$OD) δ 146.4, 142.4, 137.3, 136.4, 128.2, 126.6, 126.3, 125.0, 124.1, 119.0, 117.7, 114.9, 113.3, 112.2, 112.1, 105.6, 70.9, 65.6, 57.5, 54.4, 53.6, 30.2, 29.1, 21.4; $[\alpha]^{25}$=+33° (methylene chloride, c=1); HRMS calculated for C$_{24}$H$_{25}$N$_5$O 399.2054, found 399.2050. Anal. calcd for C$_{24}$H$_{25}$N$_5$O.1.2 H$_2$O: C, 68.45; H, 6.56; N, 16.63. Found: 68.21; H, 6.18; N, 16:82.

B. 5-Methoxycarbonyl-1-[3-(N-(2-methoxyethyl)pyrrolidin-2R-ylmethyl)indol-5-yl]-1H-benzimidazole 5-(4-Methoxycarbonyl-2-nitrophenylamino)-3-(N-(2-methoxyethyl)pyrrolidin-2R-ylmethyl)-1H-indole was used. Reduction was by catalytic hydrogenation, the cyclization reaction used ethoxymethylenemalononitrile in propanol, and the cyclization reaction was heated for 14 hours. Chromatography using 38:1:1 [ethyl acetate/methanolltriethylamine] afforded the title compound (75%) as a pale yellow foam: $^{13}$C NMR (CD$_3$OD) δ 167.4, 145.5, 142.3, 137.7, 136.3, 128.1, 126.8, 124.9, 124.7, 124.6, 121.2, 117.7, 114.7, 113.0, 112.2, 110.5, 70.6, 65.8, 57.5, 54.4, 53.5, 51.2, 30.1, 28.9, 21.4; $[\alpha]^{25}$=+63° (methylene chloride, c=1); HRMS calculated for C$_{25}$H$_{28}$, N$_4$O$_3$ 432.2163, found 432.2167.

C. 1-[3-(N-Benzyloxycarbonyl4R-methoxypyrrolidin-2R-ylmethyl)indol-5-yl]-5-cyano-1H-benzimidazole 3-(N-Benzyloxycarbonyl-4R-methoxypyrrolidin-2R-ylmethyl)-5-(4-cyano-2nitrophenylamino)-1H-indole was used. Reduction was by FeSO$_4$.7H$_2$O, the cyclization reaction used ethoxymethylenemalononitrile in propanol, and the cyclization reaction was heated for 2 hours. Chromatography using a gradient of ethyl acetate in hexanes (1:2 to 1:1 to 1:0, respectively) afforded the title compound (47%) as a pale yellow foam: R$_f$=0.15 in ethyl acetate/hexanes [1:1].

D. 5-Cyano-1-[3-(N-t-butoxycarbonylpyrrolidin-2R-ylmethyl)indol-5-yl]-1H-benzimidazole 3-(N-(t-Butoxycarbonyl)pyrrolidin-2R-ylmethyl)-5-(4-cyano-2-nitrophenylamino)-1H-indole was used. Reduction was by catalytic hydrogenation, the cyclization reaction used dimethylformamide dimethylacetal, and the cyclization reaction was heated for 24 hours. Chromatography using 25% hexanes in ether afforded the title compound (71%) as a white solid: mp, decomposes 215.0° C.; $[\alpha]^{25}$=+71° (methylene chloride, c=1); HRMS calculated for C$_{26}$H$_{27}$N$_5$O$_2$ 441.2167, found 441.2189. Anal. calcd for C$_{26}$,H$_{27}$N$_5$O$_2$.0.7 C$_6$H$_{14}$ [hexanes] 0.25 H$_2$O: C, 71.74; H, 7.50; N, 13.71. Found: C, 72.10; H, 7.10; N, 13.60.

E. 1-[3-(N-Cyclopropylmethylpyrrolidin-2R-ylmethyl)indol-5-yl]-3H-imidazo[4,5-b]pyridine 3-(N-Cyclopropylmethylpyrrolidin-2R-ylmethyl)-5-(3-nitropyrid-2-ylamino)-1H-indole was used. Reduction was by catalytic hydrogenation, the cyclization reaction used triethyl orthoformate/formic acid, and the cyclization reaction was heated for 2.5 hours. Chromatography using 9:1:0.1 [methylene chloride/methanol/ammonium hydroxide] afforded the title compound (32%) as a pale yellow foam: R$_f$=0.55 in methylene chloride/methanol/ammonium hydroxide [9:1:0.1]; $^1$H NMR (CDCl$_3$) δ 8.44 (dd, J=1.5 and 4.7 Hz, 1H), 8.39 (br s, NH), 8.33 (s, 1H), 8.16 (dd, J=1.5 and 8.1 Hz, 1H), 7.80 (d, J=1.9 Hz, 1H), 7.50–7.42 (m, 2H), 7.30 (dd, J=4.7 and 8.0 Hz, 1H), 7.12 (d, J=2.1 Hz, 1H), 3.43–3.35 (m, 1H), 3.22–3.12 (m, 1H), 2.94 (dd, J=6.1 and 12.3 Hz, 1H, 2.69–2.61 (m, 2H), 2.22–2.16 (m, 1H), 1.98 (dd, J=7.2 and 18.3 Hz, 1H), 1.81–1.51 (m, 6H), 0.99–0.88 (m, 1H), 0.58–0.43 (m, 2H); $^{13}$C NMR (CDCl$_3$) δ 147.6, 144.8, 144.3, 135.7, 128.4, 128.2, 127.0, 123.9, 118.8, 118.6, 115.3, 114.9, 112.0, 64.8, 59.9, 54.9, 30.9, 30.3, 22.2, 15.1, 10.1.

F. 5-Cyano-1-[3-(N-methylpyrrolidin-2R-ylmethyl)indol-5-yl]-1H-benzimidazole 5-(4-Cyano-2-nitrophenylamino)-3-(N-methylpyrrolidin-2R-ylmethyl)-1H-indole was used. Reduction was by catalytic hydrogenation, the cyclization reaction used ethoxymethylenemalononitrile in propanol, and the cyclization reaction was heated for 14 hours. Chromatography using 18:1:1 [ethyl acetate/methanol/triethylamine] afforded the title compound (85%) as an off-white foam: $^{13}$C NMR (DMSO-d$_6$) δ 146.9, 143.1, 137.1, 135.6, 128.1, 126.5, 126.3, 125.4, 124.9, 119.8, 117.6, 114.8, 113.1, 112.5, 112.1, 104.4, 66.1, 57.0, 40.5, 30.8, 29.1, 21.7; HRMS calculated for C$_{22}$H$_{21}$N$_5$ 355.1799, found 355.1889; $[\alpha]^{25}$=+111° (methylene chloride, c=1). Anal. calcd for C$_{22}$H$_{21}$N$_5$: C, 74.34; H, 5.96; N, 19.70. Found: C, 74.18; H, 5.61; N, 19.84.

G. 1-[3-(N-Methylpyrrolidin-2R-ylmethyl)indol-5-yl]-1H-benzimidazole 3-(N-Methylpyrrolidin-2R-ylmethyl)-5-(2-nitrophenylamino)-1H-indole was used. Reduction was by catalytic hydrogenation, the cyclization reaction used triethyl orthoformate/formic acid, and the cyclization reaction was heated for 12 hours. Chromatography using 9:1:0.1 [methylene chloride/methanol/ammonium hydroxide] afforded the title compound (43%) as a pale yellow foam: $^{13}$C NMR (CDCl$_3$) δ 143.7, 143.2, 135.9, 134.9, 128.5, 128.0, 124.6, 123.5, 122.6, 120.2, 118.6, 115.1, 114.2, 112.4, 110.8, 66.7, 57.5, 40.9, 31.5, 29.9, 21.9; $[\alpha]^{25}$=+59° (methylene chloride, c=0.4); FAB HRMS calculated for [C$_{21}$H$_{22}$N$_4$.H] 331.1925, found 331.1906.

H. 4-Methyl-1-[3-(N-methylpyrrolidin-2R-ylmethyl)indol-5-yl]-3H-imidazo[4,5-b]pyridine 5-(4-Methyl-3-nitropyrid-2-ylamino)-3-(N-methylpyrrolidin-2R-ylmethyl)-1H-indole was used. Reduction was by catalytic hydrogenation, the cyclization reaction used triethyl orthoformate/formic acid, and the cyclization reaction was heated for 12 hours. Chromatography using 12:1:0.04 [methylene chloride/methanol/ ammonium hydroxide] afforded the title compound (29%) as a pale yellow foam: $^{13}$C NMR (CDCl$_3$) δ 147.2, 144.6, 143.3, 139.8, 135.9, 135.4, 128.2, 126.8, 124.2, 119.6, 118.6, 115.2, 114.1, 112.1, 66.5, 57.4, 40.8, 31.5, 29.8, 21.8, 16.4; [α]$^{25}$=+55° (methylene chloride, c=1.2); FAB HRMS calculated for [C$_{21}$H$_{23}$N$_5$.H] 346.2034, found 346.2039.

I. 1-[3-(N-Methylprrolidin-2R-ylmethyl)indol-5-yl]-3H-imidazo[4,5-b]pyridine 3-(N-Methylpyrrolidin-2R-ylmethyl)-5-(3-nitropyrid-2-ylamino)-1H-indolewasused. Reduction was by catalytic hydrogenation, the cyclization reaction used triethyl orthoformate/formic acid, and the cyclization reaction was heated for 1.5 hours. Chromatography using 9:1:0.1 [methylene chloride/methanol/ammonium hydroxide] afforded the title compound (30%) as a white foam: $^{13}$C NMR (CDCl$_3$) δ 147.7, 144.8, 144.3, 135.8, 135.7, 128.3, 128.2, 127.0, 124.1, 118.8, 118.6, 115.3, 114.4, 112.1. 66.6, 57.5, 40.8, 31.4, 29.7, 21.8; [α]$^{25}$=+40° (methylene chloride, c=1.8); HRMS calculated for C$_{20}$H$_{21}$N$_5$ 331.1799, found 331.1786.

J. 6-Methoxy-1-[3-(N-methlpyrrolidin-2R-ylmethyl)indol-5-yl]-3H-imidazo[4,5 b]pyridine 5-(6-Methoxy-3-nitropyrid-2-ylamino)-3-(N-methylpyrrolidin-2R-ylmethyl)-1H-indole was used. Reduction was by catalytic hydrogenation, the cyclization reaction used triethyl orthoformate/formic acid, and the cyclization reaction was heated for 4 hours. Chromatography using 12:1:0.04 [methylene chloride/methanol/ammonium hydroxide] afforded the title compound (38%) as a tan foam: R$_f$=0.35 in methylene chloride/methanol/ammonium hydroxide [6:1:0.1]; $^{13}$C NMR (CDCl$_3$) δ 161.7, 144.3, 141.2, 135.4, 130.8, 130.4, 128.0, 127.5, 124.1, 117.9, 114.2, 111.9, 106.7, 66.8, 57.5, 53.7, 40.8, 31.4, 30.0, 21.8; HRMS calculated for C$_{20}$H$_{21}$N$_5$ 361.1905, found 361.1881.

K. 1-[3-(N-Methylpyrrolidin-2R-ylmethyl)indol-5-yl]-5-trifluoromethyl-1H-benzimidazole 3-(N-Methylpyrrolidin-2R-ylmethyl)-5-(4-trifluoromethyl-2-nitrophenylamino)-1H-indole was used. Reduction was by catalytic hydrogenation, the cyclization reaction used dimethylformamide dimethylacetal, and the cyclization reaction was heated for 3 hours. Chromatography using 18:1:0.1 [methylene chloride/methanol/ammonium hydroxide] afforded the title compound (49%) as a yellow foam: $^{13}$C NMR (CDCl$_3$) δ 145.0, 143.3, 136.8, 135.8, 128.5, 127.7, 124.8, 124.5, 120.3, 118.8, 118.2, 115.3, 114.5, 112.4, 111.1, 66.7, 57.5, 40.8, 31.4, 29.6, 21.9; [α]$^{25}$=+64° (methylene chloride, c=1); HRMS calculated for C$_{22}$H$_{21}$F$_3$N$_4$ 398.1720, found 398.1643. Anal. calcd for C$_{22}$H$_{21}$F$_3$N$_4$.0.1 H$_2$O: C, 66.02; H, 5.34; N, 13.99. Found: C, 65.97; H, 5.27; N, 13.61.

L. 1-[3-(2-N,N-Dimethylaminoethyl)indol-5-yl]-3H-imidazo[4,5-b]pyridine 3-(2-N,N-dimethylaminoethyl)-5-(3-nitropyrid-2-ylamino)-1H-indole was used. Reduction was by catalytic hydrogenation, the cyclization reaction used dimethylformamide dimethylacetal, and the cyclization reaction was heated for 2.5 hours. Chromatography using 9:1:0.1 [methylene chloride/methanol/ammonium hydroxide] afforded the title compound (63%) as a white foam: $^1$H NMR (CDCl$_3$) δ 9.97 (br s, NH), 8.44 (dd, J=1.4 and 4.7 Hz, 1H), 8.35 (s, 1H), 8.14 (dd, J=1.4 and 8.1 Hz, 1H), 7.76 (br s, 1H), 7.35–7.25 (m, 3H), 6.98 (d, J=2.0 Hz, 1H), 2.95–2.88 (m, 2H), 266–2.60 (m, 2H), 2.31 (s, 6H); $^{13}$C NMR (CDCl$_3$) δ 147.6, 144.8, 144.4,135.9,135.7, 128.2, 127.9, 126.8, 123.8, 118.7, 118.6, 115.0, 114.4, 112.2, 60.0, 45.3, 23.5; FAB LRMS (m/z, relative intensity) 306 ([MH]$^+$, 19), 155 (67), 135 (32), 119 (100), 103 (44).

M. 1-[3-(N-Methylpyrrolidin-2R-ylmethyl)indol-5-yl]-5phenyl-1H-benzimidazole 3-(N-Methylpyrrolidin-2R-ylmethyl)-5-(4-phenyl-2-nitrophenylamino)-1H-indole was used. Reduction was by catalytic hydrogenation, the cyclization reaction used triethyl orthoformate/formic acid, and the cyclization reaction was heated for 3 hours. Chromatography using 12:1:0.04 [methylene chloride/methanol/ammonium hydroxide] afforded the title compound (75%) as a tan foam: $^{13}$C NMR (CDCl$_3$) δ 143.8, 141.8, 136.3, 135.7, 134.3, 128.8, 128.3, 127.5, 126.8, 124.2, 123.2, 122.1, 120.7, 118.8, 118.7, 115.2, 114.7, 112.3, 110.8, 66.5, 57.5, 40.9, 31.5, 29.8, 21.9; FAB LRMS (m/z, relative intensity) 407 ([MH]$^+$, 100), 391 (9), 350 (7), 336 (14), 323 (29), 310 (7), 298 (37); FAB HRMS calculated for [C$_{27}$H$_{26}$N$_4$.H] 407.2238, found 407.2198.

N. 6,7-Dichloro-1-[3-(N-methylpyrrolidin-2R-ylmethyl)indol-5-yl]-1H-benzimidazole 5-(5,6-Dichloro-2-nitrophenylamino)-3-(N-methylpyrrolidin-2R-ylmethyl)-1H-indole was used. Reduction was by catalytic hydrogenation, the cyclization reaction used triethyl orthoformate/formic acid, and the cyclization reaction was heated for 2.5 hours. Chromatography using 12:1:0.04 [methylene chloride/methanol/ammonium hydroxide] afforded the title compound (27%) as an off-white foam: $^{13}$C NMR (CDCl$_3$) δ 146.4, 143.6, 136.3, 132.5, 128.3, 127.6, 124.7, 124.3, 121.7, 119.3, 118.5, 116.9, 114.6, 111.1, 66.5, 57.5, 40.9, 31.5, 29.9, 21.9; LRMS (m/z, relative intensity) 398 (M$^+$, 1), 314 (4), 216 (2), 84 (100); HRMS calculated for C$_{21}$H$_{20}$Cl$_2$N$_4$ 398.1068, found 398.1063.

O. 1-[3-(N-t-Butoxycarbonylpiperid-4-yl)indol-5-yl]-3H-imidazo[4,5-b]pyridine 3-(N-t-Butoxycarbonylpiperid-4-yl)-5-(3-nitropyrid-2-ylamino)-1H-indole was used. Reduction was by catalytic hydrogenation, the cyclization reaction used dimethylformamide dimethylacetal, and the cyclization reaction was heated for 12 hours. Chromatography using 5% methanol in ethyl acetate followed by recrystallization using methylene chloride afforded the title compound (39%) as a white solid: mp, 210°–218° C.; R$_f$=0.60 in 5% methanol in ethyl acetate; FAB LRMS (m/z, relative intensity) 418 ([MH$^+$, 94), 362 (100), 318 (65), 261 (38), 235 (35). Anal. calcd for C$_{24}$H$_{27}$N$_5$O$_2$: C, 69.04; H, 6.52; N, 16.77. Found: C, 68.72; H, 6.90; N, 16.59.

P. 1-[3-(N-Methylpyrrolidin-3-yl)indol-5-yl]-3H-imidazo[4,5-b]pyridine 3-(N-Methylpyrrolidin-3-yl)-5-(3-nitropyrid-2-ylamino)-1H-indole was used. Reduction was by catalytic hydrogenation, the cyclization reaction used dimethylformamide dimethylacetal, and the cyclization reaction was heated for 24 hours. Chromatography using 9:1:1 [ethyl acetate/methanol/triethylamine] afforded the title compound (24%) as a white solid: mp, 110.0°–112.0° C.; $^{13}$C NMR (CDCl$_3$) δ 147.7, 144.8, 144.3, 136.2, 135.7, 128.3, 127.3, 126.8, 122.4, 119.0, 118.7,115.6, 112.4, 62.3, 56.2, 42.2, 34.9, 32.1. HRMS calculated for C$_{19}$H$_{19}$N$_5$ 317.1643, found 317.1665. Anal. calcd for C$_{19}$H$_{19}$N$_5$.0.5 C$_4$H$_8$O$_4$ [ethyl acetate].0.5 H$_2$O: C, 68.08; H, 6.53; N, 18.90. Found: C, 67.93; H, 6.51; N, 19.17.

Q. 1-[3-(N-(2,2,2-Trichloroethoxycarbonyl)pyrrolidin-2R-ylmethyl)indol-5-yl]-3H-imidazo[4,5-b]pyridine 5-(3-Nitropyrid-2-ylamino)-3-(N-(2,2,2-trichloroethoxycarbonyl)pyrrolidin-2R-ylmethyl)-1-H-indole was used. Reduction was by catalytic hydrogenation, the cyclization reaction used triethyl orthoformate/formic acid, and the cyclization reaction was heated for 3.5 hours. Chromatography using 10% methanol in methylene chloride afforded the title compound (17%) as a tan foam: R$_f$=0.50 in 5% methanol in methylene chloride.

R. 5-Chloro-1-[3-(N-methylpyrrolidin-2R-ylmethyl)indol-5-yl]-1H-benzimidazole

5(4-Chloro-2-nitrophenyl)amino-3-(N-methylpyrrolidin-2R-ylmethyl)-1H-indole was used. Reduction was by catalytic hydrogenation, the cyclization reaction used triethyl orthoformate/formic acid, and the cyclization reaction was heated for 4.5 hours. Chromatography using 12:1:0.4 [methylene chloride/methanol/ammonium hydroxide] afforded the title compound (34%) as an off-white solid: R$_f$=0.35 in 9:1:0.1 [methylene chloride/methanol/ammonium hydroxide]; FAB HRMS calculated for [C$_{21}$H$_{21}$, ClN$_4$.H]$^+$ 365.1535, found 365.1535; [α]$^{25}$=+61° (methylene chloride, c=0.29).

S. 6-Chloro-1-[3-(N-methylpyrrolidin-2R-ylmethyl)indol-5-yl]-1H-benzimidazole 5-(5-Chloro-2-nitrophenyl)amino-3-(N-methylpyrrolidin-2R-ylmethyl)-1H-indole was used. Reduction was by catalytic hydrogenation, the cyclization reaction used triethyl orthoformate/formic acid, and the cyclization reaction was heated for 4.5 hours. Chromatography using 12:1:0.4 [methylene chloride/methanol/ammonium hydroxide] afforded the title compound (28%) as a light yellow solid: R$_f$=0.35 in 9:1:0.1 [methylene chloride/methanol/ammonium hydroxide]; FAB HRMS calculated for [C$_{21}$H$_{21}$ClN$_4$.H]+365.1535, found 365.1513; [α]$^{25}$=+57° (methylene chloride, c=0.27).

T. 7-Chloro-1-[3-(N-methylpyrrolidin-2R-ylmethyl)indol-5-yl]-1H-benzimidazole 5-(6-Chloro-2-nitrophenyl)amino-3-(N-methylpyrrolidin-2R-ylmethyl)-1H-indole was used. Reduction was by catalytic hydrogenation, the cyclization reaction used triethyl orthoformate/formic acid, and the cyclization reaction was heated for 4.5 hours. Chromatography using 12:1:0.4 [methylene chloride/methanol/ammonium hydroxide] afforded the title compound (28%) as a light yellow solid: R$_f$=0.35 in 9:1:0.1 [methylene chloride/methanol/ammonium hydroxide]; FAB HRMS calculated for [C$_{21}$H$_{21}$ClN$_4$.H]$^+$365.1535, found 365.1504; [α]$^{25}$=+45° (methylene chloride, c=1.36).

U. 5-Cyano-1-[3-(N-t-butoxycarbonylpiperid-4-yl)indol-5-yl]-1H-benzimidazole 5-(4-Cyano-2-nitrophenyl)amino-3-(N-t-butoxycarbonyl-1,2,5,6-tetrahydropyrid-4-yl)-1H-indole was used. Reduction was by catalytic hydrogenation, the cyclization reaction used ethoxymethylene malononitrile, and the cyclization reaction was heated for 48 hours. Chromatography using 10% ethyl acetate in methylene chloride afforded the title compound (10%) as a brown foam: R$_f$=0.2 in 10% ethyl acetate in methylene chloride; HRMS calculated for C$_{26}$H$_{27}$N$_5$O$_2$ 441.2167, found 441.2169.

V. 5-Cyano-1-[3-(N-t-butoxycarbonyl-1,2,5,6-tetrahydropyrid-4-yl)indol-5-yl]-1H-benzimidazole 5-(4-Cyano-2-nitrophenyl)amino-3-(N-t-butoxycarbonyl-1,2,5,6-tetrahydropyrid-4-yl)-1H-indole was used. Reduction was by aqueous FeSO$_4$ in ethanol, the cyclization reaction used ethoxymethylene malononitrile, and the cyclization reaction was heated for 56 hours. Chromatography using 5% acetone in methylene chloride afforded the title compound (10%) as a brown foam: R$_f$=0.5 in 5% acetone in methylene chloride; HRMS calculated for C$_{26}$H$_{25}$N$_5$O$_2$ 439.2011, found 439.1999.

W. 5-Cyano-1-[3-(N-methylpyrrolidin-3-yl)indol-5-yl]-1H-benzimidazole 5-(4-Cyano-2-nitrophenyl)amino-3-(N-methylpyrrolidin-3-yl)-1H-indole was used. Reduction was by catalytic hydrogenation, the cyclization reaction used triethyl orthoformate/formic acid, and the cyclization reaction was heated for 2 hours. Chromatography using 9:1:0.5 [methylene chloride/methanol/ammonium hydroxide] afforded the title compound (22%) as a light yellow solid: R$_f$=0.35 in 9:1:0.1 [methylene chloride/methanol/ammonium hydroxide]; $^{13}$C NMR (CDCl$_3$) δ 145.7, 143.3, 137.5, 136.5, 127.5, 126.8, 126.7, 125.4, 123.0, 120.3, 119.9, 118.5, 115.8, 112.7, 111.9, 105.7, 62.8, 56.3, 42.3, 35.0, 32.3; FAB LRMS (m/z, relative intensity) 342 (MH$^+$).

X. 5-Cyano-1-[3-(N-methylpyrrolidin-2R-ylmethyl)indol-5-yl]-1H-pyrido[4,5-b]imidazole 5-(5-Cyano-3-nitropyrid-2-yl)amino-3-(N-methylpyrrolidin-2R-ylmethyl)-1H-indole was used. Reduction was by catalytic hydrogenation, the cyclization reaction used triethyl orthoformate/formic acid, and the cyclization reaction was heated for 2.5 hours. Chromatography using 12:1:0.4 [methylene chloride/methanol/ammonium hydroxide] afforded the title compound (50%) as a light yellow solid: R$_f$=0.2 in 12:1:0.4 [methylene chloride/methanol/ammonium hydroxide]; $^{13}$C NMR (CDCl$_3$) δ 149.3, 147.7, 147.0, 136.0, 134.8, 131.9, 128.4, 125.8, 124.4, 118.4, 117.7, 115.3, 114.6, 112.3, 104.1, 66.6, 57.5, 40.8, 31.4, 29.7, 21.9; HRMS calculated for C$_{21}$H$_{20}$N$_6$ 356.1752, found 356.1784; [α]$^{25}$=+78° (methylene chloride, c=0.48). Anal. calcd for C$_{21}$H$_{20}$N$_6$.0.5 H$_2$O: C, 69.07; H, 5.80; N, 23.01. Found: C, 69.11; H, 5.82; N, 22.62.

Y. 5-Methyl-1-[3-(N-methylpyrrolidin-2R-ylmethyl)indol-5-yl]-1H-benzimidazole 5-(4-Methyl-2-nitrophenyl)amino-3-(N-methylpyrrolidin-2R-ylmethyl)-1H-indole was used. Reduction was by catalytic hydrogenation, the cyclization reaction used ethoxymethylene malononitrile, and the cyclization reaction was heated for 24 hours. Chromatography using 8:1:1 [ethyl acetate/methanol/triethylamine] afforded the title compound (21%) as a brown foam: R$_f$=0.3 in 8:1:1 [ethyl acetate/methanol/triethylamine]; $^{13}$C NMR (CD$_3$OD) δ 143.1, 143.0, 136.1, 132.6, 132.4, 127.9, 127.6, 124.9, 124.8, 118.5, 117.8, 114.2, 112.4, 112.2, 110.1, 67.3, 56.8, 39.4, 30.7, 28.3, 21.0, 20.1; LRMS (m/z, relative intensity) 344 (M$^+$, 38), 334 (10), 318 (100), 289 (18); HRMS calculated for C$_{22}$H$_{24}$N$_4$ 344.2003, found 344.2030.

EXAMPLE 2

General Procedure for the Alkylation of Pyrrolidines

To a stirred solution of the pyrrolidine derivative (1.00 mmol) and triethylamine (0.126 g, 1.25 mmol, 1.25 eq) or sodium carbonate (0.132 g, 1.25 mmol, 1.25 eq) in either anhydrous methylene chloride, anhydrous acetonitrile, absolute ethanol, or i-propanol (10 mL) at room temperature under nitrogen was added dropwise the alkylating agent (1.25 mmol, 1.25 eq). The resulting reaction solution was then stirred under nitrogen at room temperature or heated at reflux for 1–20 hours, depending on substrate. The resulting reaction mixture was directly column chromatographed using silica gel (approximately 25 g) and elution with methylene chloride: methanol: ammonium hydroxide [9:1:0.1] to afford the appropriate alkylated pyrrolidine.

Following this procedure the following compounds were prepared.

A. 3-(N-Cyclopropymethldpyrrolidin-2R-ylmethyl)-5-(3-nitropyrid-2-yl-amino)-1H-indole 3-(Pyrrolidin-2R-ylmethyl)-5-(3-nitropyrid-2-yl-amino)-1H-indole was used, and the alkylating agent was bromomethyl cyclopropane. Triethylamine was the base, methylene chloride was the reaction solvent, and the reaction solution was heated at reflux for 4 hours. Chromatography afforded the title compound (34%) as a dark red foam: $^{13}$C NMR (CDCl$_3$) δ 155.7, 151.4, 135.5, 134.3, 129.4, 128.2, 123.1, 119.3, 114.4, 114.3, 113.0, 111.4, 65.0, 59.9, 55.0, 30.9, 30.3, 22.2, 10.0; FAB LRMS (m/z, relative intensity) 392 (MH$^+$, 33), 374 (3), 307 (3), 267 (7), 220 (7), 154 (10), 124 (100); HRMS calculated for C$_{22}$H$_{25}$N$_5$O$_2$ 391.2011, found 391.1988.

B. 5-(2,5-Dimethyl-1H-pyrrol-1-yl)-3-(N-(2-methoxyethyl) pyrrolidin-2R-ylmethyl)-1H-indole 5-(2,5-Dimethyl-1H-pyrrol-1-yl)-3-(pyrrolidin-2R-ylmethyl)-1H-indole was used. The alkylating agent was bromoethyl methyl ether and sodium iodide. Sodium carbonate was the base, N,N-dimethylformamide was the reaction solvent, and the reaction solution was heated at 120° C. for 2 hours. Chromatography afforded the title compound (54%) as an off-white foam: R$_f$=0.75 in methylene chloride/methanol/ammonium hydroxide [9:1:0.1]; LRMS (m/z, relative intensity) 351 (M$^+$, 48), 304 (10), 210 (57), 128 (100); HRMS calculated for C$_{22}$H$_{29}$N$_3$O 351.2313, found 351.2262.

C. 5-Cyano-1-[3-(N-(2-methoxyethyl)-4R-methoxypyrrolidin-2R-ylmethyl)indol-5-yl]-1H-benzimidazole 5-Cyano-1-[3-(4R-methoxypyrrolidin-2R-ylmethyl) indol-5-yl]-1H-benzimidazole was used. The alkylating agent was bromoethyl methyl ether and sodium iodide. Sodium carbonate was the base, N,N-dimethylformamide was the reaction solvent, and the reaction solution was heated at 130° C. for 2 hours. Chromatography afforded the title compound (60%) as an off-white foam: R$_f$=0.60 in methylene chloride/methanol/ammonium hydroxide [9:1:0.1]; $^{13}$C NMR (CDCl$_3$) δ 145.6, 143.3, 37.5, 135.8, 128.6, 127.2, 126.7, 125.6, 124.7, 119.8, 118.6, 115.5, 114.3, 112.5, 111.9, 105.8, 78.8, 71.6, 64.5, 60.0, 58.8, 56.5, 53.5, 37.9, 29.4; [α]$^{25}$=+61° (methanol, c=0.53); FAB HRMS calculated for [C$_{25}$H$_{27}$N$_5$O$_2$.H] 430.2245, found 430.2222.

D. 5-Cyano-1-[3-(N-cyclopropylmethyl)pyrrolidin-2R-ylmethyl)indol-5-yl]-1H-benzimidazole 5-Cyano-1-[3-(pyrrolidin-2R-ylmethyl)indol-5-yl]-1H-benzimidazole was used. The alkylating agent was (bromomethyl)cyclopropane and sodium iodide. Sodium carbonate was the base, N,N-dimethylformamide was the reaction solvent, and the reaction solution was heated at reflux for 2 hours. Chromatography afforded the title compound (59%) as a pale yellow foam: R$_f$=0.40 in methylene chloride/methanol/ammonium hydroxide [9:1:0.1]; $^{13}$C NMR (CDCl$_3$) δ 146.4, 142.4, 137.2, 136.5, 127.4, 126.9, 126.7, 126.0, 124.1, 119.0, 118.4, 114.7, 112.7, 112.2, 109.9, 105.6, 67.8, 58.8, 54.1, 29.5, 26.7, 21.3, 6.7; [α]$^{25}$=−29° (methylene chloride, c=0.5); FAB LRMS (m/z, relative intensity) 396 ([MH$^+$], 100), 309 (21), 273 (9); FAB HRMS calculated for [C$_{25}$H$_{25}$N$_5$.H] 396.2191, found 396.2191.

EXAMPLE 3

General Method for the Conversion of N-Benzyloxycarbonylpyrrolidines to NH-Pyrrolidines A mixture of the N-benzyloxycarbonylpyrrolidine (10.0 mmol) and 20% palladium hydroxide on carbon (1.00 g) in absolute ethanol (50 mL) was shaken under a hydrogen atmosphere (3 atm) at room temperature for a time depending on the substrate. The resulting reaction mixture was filtered through Celite®, and the filtrate was evaporated under reduced pressure. The residue was either used directly as the appropriate NH-pyrrolidine, or the residue was purified by column chromatography using silica gel (approximately 100 g) and eluting with an appropriate solvent system to afford the desired NH-pyrrolidine.

Following this procedure the following compounds were prepared.

A. 5-(2,5-Dimethyl-1H-pyrrol-1-yl)-3-(pyrrolidin-2R-ylmethyl)-1H-indole

5(2,5-Dimethyl-1H-pyrrol-1-yl)-3-(N-benzyloxycarbonylpyrrolidin-2R-ylmethyl)-1H-indole was used, and the reaction time was 18 hours. The filtrate was evaporated under reduced pressure to afford the title compound (100%) as a pale yellow foam: R$_f$=0.35 in methylene chloride/methanol/ammonium hydroxide [9:1:0.1]; $^{13}$C NMR (CDCl$_3$) δ 135.8, 130.6, 129.4, 128.5, 127.8, 127.0, 124.6, 122.0, 118.1, 112.7, 111.9, 105.2, 59.8, 45.7, 31.5, 30.6, 24.9, 13.3.

B. 5-Cyano-1-[3-(4R-methoxypyrrolidin-2R-ylmethyl) indol-5-yl]-1H-benzimidazole

1-[3-(N-Benzyloxycarbonyl-4R-methoxypyrrolidin-2R-ylmethyl)indol-5-yl]-cyano-1H-benzimidazole was used, and the reaction time was 24 hours. Column chromatography eluting with methylene chloride/methanol/ammonium hydroxide [12:1:0.04] afforded the title compound (44%) as a pale yellow amorphous solid: R$_f$=0.35 in methylene chloride/methanol/ammonium hydroxide [9:1:0.1]; $^{13}$C NMR (CDCl$_3$) δ 145.7, 143.3, 137.5, 136.1, 128.3, 127.0, 126.7, 125.4, 125.0, 119.8, 118.4, 115.3, 114.1, 112.6, 111.9, 105.7, 82.1, 59.1, 56.5, 52.4, 38,7, 31.6; HRMS calculated for [C$_{22}$H$_{21}$N$_5$O.H] 372.1827, found 372.1825.

EXAMPLE 4

General Method for the Conversion of N-t-Butoxycarbonylamines to NH-Amines

To a stirred solution of the N-t-butoxycarbonylamine (2.00 mmol) in an appropriate anhydrous solvent (10 mL) at 0° C. was added dropwise a solution of hydrogen chloride in dioxane (4.0M, 2 mL, 8.0 mmol, 4 eq). The resulting reaction mixture was then stirred at room temperature under nitrogen for 12 hours, and the precipitated solid was filtered to afford the appropriate NH-amine as its hydrochloride salt.

Following this procedure the following compounds were prepared.

A. 5-Cyano-1-[3-(pyrrolidin-2R-ylmethyl)indol-5-yl]-1H-benzimidazole

5-Cyano-1-[3-(N-t-butoxycarbonylpyrrolidin-2R-ylmethyl)indol-5-yl]-1H-benzimidazole was used, and methylene chloride was used as the solvent. Filtration afforded the title compound (83%) as white solid: mp, decomposes 185° C.; LRMS (m/z, relative intensity) 341 (M$^+$, 4), 339 (60), 272 (73), 70 (100); HRMS calculated for C$_{21}$H$_{19}$N$_5$ 341.1643, found 341.1649.

B. 1-[3-(Piperid-4-yl)indol-5-yl]-3H-imidazo[4,5-b] pyridine

1-[3-(N-t-Butoxycarbonylpiperid-4-yl)indol-5-yl]-3H-imidazo[4,5-b]pyridine was used, and methylene chloride was used as the solvent. Filtration afforded the title compound (100%) as a yellow solid: mp 260°–268° C. with effervescence; $^{13}$C NMR (CD$_3$OD) δ 149.7, 145.6, 144.0, 138.5, 127.7, 126.0, 125.8, 125.5, 124.6, 123.9, 120.6, 119.7, 117.4, 113.7, 45.7, 32.6, 30.7; FAB LRMS (m/z, relative intensity) 318 (M$^+$, 22), 277 (12), 261 (4), 235 (5), 185 (100).

C. 5-Cyano-1-[3(piperid-4-yl)indol-5-yl]-1H-benzimidazole

5-Cyano-1-[3-(N-t-butoxycarbonylpiperid-4-yl)indol-5-yl]-1H-benzimidazole was used, and methylene chloride was used as solvent. Filtration afforded the title compound (64%) as a yellow solid: IR (KBr) 2229 cm$^{-1}$; $^{13}$C NMR (CD$_3$OD) δ 137.4, 129.6, 126.6, 124.7, 123.6, 120.6, 119.2, 117.9, 117.5, 116.4, 114.8, 112.8, 109.9, 44.6, 31.3, 29.4. Anal. calcd. for C$_{21}$H$_{19}$N$_5$.3 HCl.1.25 H$_2$O: C, 53.29; H, 5.22; N, 14.80. Found: C, 53.63; H, 5.34; N, 14.68.

D. 5-Cyano-1-[3-(1,2,5,6-tetrahydropyrid-4-yl)indol-5-yl]-1H-benzimidazole

5-Cyano-1-[3-(N-t-butoxycarbonyl-1,2,5,6-tetrahydropyrid-4-yl)indol-5-yl]-1H-benzimidazole was used, and methylene chloride was used as solvent. Filtration afforded the title compound (75%) as a yellow solid: mp, decomposes at 240° C.; IR (KBr) 2228 cm$^{-1}$; $^{13}$C NMR (CD$_3$OD) δ 144.4, 137.9, 133.6, 131.1, 129.9, 126.0, 125.3, 125.2, 120.1, 118.4, 118.3, 117.5, 117.3, 116.1, 114.8, 113.2, 112.9, 110.4, 66.7, 42.0, 40.9. Anal. calcd. for C$_{21}$H$_{17}$N$_5$.1.1 C$_4$H$_8$O$_2$ [dioxane].1.1 HCl: C, 64.03; H, 5.69; N, 14.70. Found: C, 64.20; H, 5.54; N, 14.47.

EXAMPLE 5

5-Hydroxymethyl-1-[3-(N-(2-methoxyethyl) pyrrolidin-2R-ylmethyl)indol-5-yl]-1H-benzimidazole To a stirred mixture of lithium aluminum hydride (0.081 g, 2.13 mmol, 3 eq) in anhydrous tetrahydrofuran (6 mL) was added a solution of 5-methoxycarbonyl-1-[3-(N-(2-methoxyethyl) pyrrolidin-2R-ylmethyl)indol-5-yl]-1H-benzimidazole (0.31 g, 0.72 mmol) in anhydrous tetrahydrofuran (4 mL). The resulting reaction mixture was stirred at room temperature under nitrogen for 1 hour. Sodium sulfate decahydrate (5 g) was then added cautiously, followed by water (0.1 mL) and ethyl acetate (10 mL). The resulting mixture was stirred at room temperature for 1 hour. The mixture was then filtered through Celite®, and the filtrate was evaporated under reduced pressure to afford the title compound (0.19 g, 65%) as a pale brown foam: R$_f$=0.40 in ethyl acetate/methanol/triethylamine [18:1:1]; $^{13}$C NMR (CD$_3$OD) δ 143.6, 142.8, 136.4, 136.1, 133.8, 128.1, 127.3, 124.7, 123.0, 117.7, 117.4, 114.5, 113.1, 112.1, 110.4, 70.8, 65.6, 64.1, 57.5, 54.4, 53.5, 30.2, 29.1, 21.4; HRMS calculated for C$_{24}$H$_{28}$N$_4$O$_2$ 404.2214, found 404.2121.

EXAMPLE 6

1-[3-(2-Aminoethyl)indol-5-yl]-3H-imidazo[4,5-b]pyridine

To a stirred mixture of lithium aluminum hydride (0.22 g, 5.80 mmol, 5 eq) in anhydrous tetrahydrofuran (10 mL) was added 5-[3-(2-nitroethenyl)indol-5-yl]-1H-benzimidazole (0.35 g, 1.14 mmol) as a solid portionwise rapidly. The resulting reaction mixture was stirred at room temperature under nitrogen for 12 hours. Sodium sulfate decahydrate (10 g) was then added carefully to the reaction mixture, followed by water (0.5 mL) and ethyl acetate (25 mL). The resulting reaction mixture was vigorously stirred at room temperature under nitrogen for 1 hour. The reaction mixture was then filtered through Celite®, and the filtrate was evaporated under reduced pressure. The residue was column chromatographed using silica gel (approximately 30 g) and elution with ethyl acetate/methanol/triethylamine/ammonium hydroxide [8:1:1:0.1] to afford the title compound (41%) as a clear, colorless oil: R$_f$=0.10 in ethyl acetate/methanol/triethylamine/ammonium hydroxide [8:1:1:0.1]. This oil was dissolved in methylene chloride/methanol [4 mL/0.5 mL, respectively], and maleic acid (0.050 g, 0.43 mmol) was added to this solution. The resulting solid was filtered to afford the title compound as its maleate salt (0.085 g): mp, 195.0°–196.0° C. with effervescence; $^1$H NMR (DMSO-d$_6$) δ 11.3 (br s, NH), 8.81 (s, 1H), 8.42 (dd, J=1.4 and 4.7 Hz, 1H), 8.22 (dd, J=1.4 and 8.0 Hz, 1H), 7.97 (d, J=1.7 Hz, 1H), 7.78 (br s, 2H), 7.61–7.52 (m, 2H), 7.43 –7.36 (m, 2H), 6.04 (s, 2H), 3.37 (br s, 2H), 3.16–3.01 (m, 4H); Anal. calcd for C$_{16}$H$_{15}$N$_5$C$_4$H$_4$O$_4$ [maleic acid].0.1 H$_2$O: C, 60.78; H, 4.89; N, 17.72. Found: C, 60.58; H, 4.53; N, 17.50.

EXAMPLE 7

1-[3-(Pyrrolidin-2R-ylmethyl)indol-5-yl]-3H-imidazo[4,5-b]pyridine

A mixture of 1-[3-(N-(2,2,2-trichloroethoxycarbonyl) pyrrolidin-2R-ylmethyl)indol-5-yl]-3H-imidazo[4,5-b] pyridine (0.090 g, 0.18 mmol) and zinc dust (0.45 g) in a solution of tetrahydrofuran (2 mL) and aqueous KH$_2$PO$_4$ (1.0M, 1 mL) was stirred at room temperature for 12 hours. Sodium carbonate (0.35 g) was then added to the reaction mixture, and the resulting mixture was filtered through Celite® with copious washing with ethanol. The combined filtrates were evaporated under reduced pressure, and the residue was column chromatographed using silica gel (approximately 1 g) and elution with methylene chloride/methanol/ammonium hydroxide [6:1:0.1] to afford the title compound (0.022 g, 40%) as an amorphous white solid: $^1$H NMR (CDCl$_3$) δ 9.20 (br s, NH), 8.44 (dd, J=1.4 and 4.8 Hz, 1H), 8.31 (s, 1H), 8.15 (dd, J=1.4 and 8.1 Hz, 1H), 7.80 (d, J=1.7 Hz, 1H), 7.44 (d, J=8.5 Hz, 1H), 7.38 (dd, J=1.9 and 8.6 Hz, 1H), 7.29 (dd, J=4.8 and 8.1 Hz, 1H), 7.07 (s, 1H), 3.38–3.30 (m, 1H), 3.06–2.80 (m, 4H), 2.48 (br s, NH), 1.95–1.64 (m, 3H), 1.49–1.40 (m,1H); LRMS (m/z, relative intensity) 317 (M$^+$, 1), 315 (25), 248 (100), 129 (39), 70 (80); HRMS calculated for C$_{19}$H$_{19}$N$_5$ 317.1643 found 317.1659.

EXAMPLE 8

General Synthesis of 5-(2-Nitroarylamino)-1H-indoles

A solution of the 5-amino-1H-indole (2.00 mmol), a 2-nitrohaloarene (3.00 mmol, 1.5 eq), and a base (if needed, 3.00 mmol) in an appropriate anhydrous solvent (10 mL) was either heated at reflux under nitrogen for 1–18 hours, depending on substrate, or stirred at room temperature for 1 hour, depending on substrate. The reaction was evaporated under reduced pressure, and the residue was column chromatographed using silica gel (approximately 50 g) and elution with methylene chloride: methanol: ammonium hydroxide [9:1:0.1] or another appropriate solvent system to afford the 5-aryl-1H-indole derivative. In some cases recrystallization of the solid obtained from chromatography was performed to obtained analytically pure samples of the appropriate 5-(2-nitroarylamino)-1H-indole.

Following this procedure the following compounds were prepared.

A. 5-(4-Cyano-2-nitrophenylaminol-3-(N-(2-methoxyethyl) pyrrolidin-2R-ylmethyl)-1H-indole 5-Amino-3-(N-(2-methoxyethyl)pyrrolidin-2R-ylmethyl) -1H-indole and 4-chloro-3-nitrobenzonitrile were used. Triethylamine was used as base, absolute ethanol was used as solvent, and the reaction was heated at reflux for 2 hours. Column chromatography using ethyl acetate/methanol/triethylamine [18:1:1] afforded the title compound (74%) as a red foam: R$_f$=0.55 ethyl acetate/methanol/triethylamine [18:1:1]; $^{13}$C NMR (CD$_3$OD) δ 148.8, 138.0, 137.1, 132.9, 132.7, 129.8, 129.6, 125.6, 121.0, 119.1, 118.3, 117.6, 114.2, 113.6, 99.4, 72.2, 67.2, 59.0, 55.9, 55.0, 31.6, 30.5, 22.9. Anal. calcd for $C_{23}H_{25}N_5O_3 \cdot 0.5\ H_2O$: C, 64.47; H, 6.11; N, 16.34. Found: C, 64.33; H, 5.94; N, 16.19.

B. 5-(4-Methoxycarbonyl-2-nitrophenylamino)-3-(N-(2-methoxyethly)pyrrolidin-2R-ylmethyl)-1H-indole 5-Amino-3-(N-(2-methoxyethyl)pyrrolidin-2R-ylmethyl)-1H-indole and methyl 4-chloro-3-nitrobenzoate were used. Triethylamine was used as base, absolute ethanol was used as solvent, and the reaction was heated at reflux for 2 hours. Column chromatography using ethyl acetate/methanol/triethylamine [34:1:1] afforded the title compound (88%) as a red foam: $R_f$=0.60 in ethyl acetate/methanol/triethylamine [18:1:1]; $^{13}$C NMR (CD$_3$OD) δ 165.5, 147.7, 135.5, 134.9, 131.1, 128.6, 128.5, 128.3, 124.1, 119.7, 117.3, 116.0, 115.6, 112.7, 112.1, 70.7, 65.8, 57.5, 54.4, 53.6, 51.2, 30.2, 29.1, 21.4; HRMS calculated for $C_{24}H_{27}N_4O_5$ 452.2061, found 452.1965. Anal. calculated for $C_{24}H_{27}N_4O_5$: C, 63.08; H, 6.29; N, 12.26. Found: C, 63.12; H, 6.38; N, 12.16.

C. 3-(N-Benzyloxvcarbonyl-4R-methoxvpyrrolidin-2R-ylmethyl)-5-(4-cyano-2-nitrophenylamino)-1H-indole 5-Amino-3-(N-benzyloxycarbonyl-4R-methoxypyrrolidin-2R-ylmethyl)-1H-indole and 4-chloro-3-nitrobenzonitrile were used. Triethylamine was used as base, absolute ethanol was used as solvent, and the reaction was heated at reflux for 3.5 hours. Column chromatography using ethyl acetate/hexanes [1:3] afforded the title compound (70%) as a red foam: $R_f$=0.45 in ethyl acetate/hexanes [1:1].

D. 3-(N-t-Butoxycarbonylpyrrolidin-2R-ylmethyl)-5-(4-cyano-2-nitrophenylamino)-1H-indole 5-Amino-3-(N-t-butoxycarbonylpyrrolidiny-2R-ylmethyl)-1H-indole and 4-chloro-3-nitrobenzonitrile were used. Triethylamine was used as base, absolute ethanol was used as solvent, and the reaction was heated at reflux for 3 hours. Column chromatography using methylene chloride/methanol/ammonium hydroxide [18:1:0.1] afforded the title compound (82%) as a red foam: mp, decomposes 60° C.; IR (KBr) 2226, 1688, 1681, 1671, 1621 cm$^{-1}$; LRMS (m/z, relative intensity) 461 (M$^+$, 23), 431 (27), 388 (13), 291 (50), 244 (43), 170 (53), 114 (75), 70 (100); HRMS calculated for $C_{25}H_{27}N_5O_4$ 461.2065, found 461.2071.

E. (R)-5-(3-Nitropyrid-2-ylamino)-3-(pyrrolidin-2-ylmethyl)-1H-indole (R)-5-Amino-3-(pyrrolidin-2-ylmethyl)indole and 2-chloro-3-nitropyridine were used. Sodium acetate was used as base, acetic acid was used as solvent, and the reaction was heated at reflux (116°0 C.) for 2 hours. Column chromatography afforded the title compound (23%) as a dark red foam: $^1$H NMR (CDCl$_3$) δ 10.05 (br s, 1H), 9.23 (br s, 1H), 8.49 (dd, J=1.8 and 8.3 Hz, 1H), 8.39 (1.8 and 4.5 Hz, 1H), 7.70 (d, J=1.7 Hz,1H), 7.33–7.22 (m, 2H), 6.98 (s,1H), 6.73 (dd, J=4.5 and 8.3 Hz, 1H), 3.46–3.34 (m, 1H), 3.10–2.97 (m, 1H), 2.97–2.78 (m, 3H), 1.99–1.64 (m, 3H), 1.56–1.42 (m, 1H); $^{13}$C NMR (CDCl$_3$) δ 155.7, 151.5, 135.5, 134.5, 129.2, 128.1, 127.8, 123.8, 119.4, 114.3, 113.0, 111.6, 59.5, 45.7, 31.3, 30.6, 24.7; FAB LRMS (m/z, relative intensity) 338 (6, [MH$^+$]), 309 (12), 155 (49), 135 (38), 119 (100). Anal. calcd for $C_{18}H_{19}N_5O_2 \cdot 0.67\ C_2H_4O_2$ [acetic acid]: 61.53; H, 5.79; N, 18.56. Found: C, 61.57; H, 5.74; N, 18.82.

F. 5-(4-Cyano-2-nitrophenylamino)-3-(N-methylpyrrolidin-2-ylmethyl)-1H-indole (R)-5-Amino-3-(N-methylpyrrolidin-2-ylmethyl)-1H-indole and 4-chloro-3-nitrobenzonitrile were used. Triethylamine was used as base, absolute ethanol was used as solvent, and the reaction was heated at reflux for 4 hours. Column chromatography afforded the title compound (80%) as a red solid: mp, 170.0°–171.0° C.; $^{13}$C NMR (CDCl$_3$) δ 147.3,137.1, 135.4, 132.0, 131.4, 128.6, 128.0, 125.3, 120.6, 117.9, 117.1, 116.3, 113.1, 111.9, 99.1, 68.1, 57.3, 40.6, 31.2, 28.1, 21.9. Anal. calcd for $C_{21}H_{21}N_5O_2 \cdot 0.05\ CH_2Cl_2$: C, 66.59; H, 5.60; N, 18.44. Found: C, 66.56; H, 5.26; N, 18.42.

G. 3-(N-Methylpyrrolidin-2-ylmethyl)-5-(2-nitrophenylamino)-1H-indole (R)-5-Amino-3-(N-methylpyrrolidin-2-ylmethyl)-1H-indole and o-nitrofluorobenzene were used. Triethylamine was used as base, o-nitrofluorobenzene was used as solvent, and the reaction was heated at reflux for 24 hours. Column chromatography afforded the title compound (48%) as a red amorphous solid: $^1$H NMR (CDCl$_3$) δ 9.62 (br s, NH), 8.77 (br s, NH), 8.19 (dd, J=8.7 and 1.5 Hz,1H), 7.47 (d, J=1.6 Hz, 1H), 7.38 (d, J=8.5 Hz, 1H), 7.29–7.23 (m, 1H), 7.09–7.00 (m, 3H), 6.69–6.64 (m, 1H), 3.20–3.12 (m, 2H), 2.63 (dd, J=14.0 and 9.5 Hz, 1H), 2.54–2.45 (m, 1H), 2.45 (s, 3H), 2.25 (dd, J=17.1 and 9.2 Hz, 1H), 1.91–1.54 (m, 4H); $^{13}$C NMR (CDCl$_3$) δ 145.4, 135.7, 134.8, 132.1, 130.1, 128.6, 126.5, 123.6, 120.7, 116.4, 116.4, 116.1, 114.1, 112.2, 66.7, 57.5, 40.8, 31.5, 29.8, 21.9; FAB HRMS calculated for [$C_{20}H_{22}N_4O_2$.H] 351.1823, found 351.1797.

H. 5-(4-Methyl-3-nitropyrid-2-ylamino)-3-(N-methylpyrrolidin-2-ylmethyl)-1H-indole (R)-5-Amino-3-(N-methylpyrrolidin-2-ylmethyl)-1H-indole and 2-chloro-4-methyl-3-nitropyridine were used. Triethylamine was used as base, absolute ethanol was used as solvent, and the reaction was heated at reflux for 24 hours. Column chromatography afforded the title compound (34%) as a red amorphous solid: $^1$H NMR (CDCl$_3$) δ 9.26 (br s, NH), 8.79 (br s, NH), 8.10 (d, J=4.8 Hz, 1H), 7.64 (d, J=1.7 Hz, 1H), 7.29 (d, J=8.5 Hz, 1H)), 7.17 (dd, J=8.5 and 1.9 Hz, 1H), 6.97 (d, J=2.2 Hz, 1H), 6.56 (d, J=4.8 Hz, 1H), 3.25–3.16 (m, 2H), 2.67 (dd, J=13.2 and 9.4 Hz, 1H), 2.64–2.56 (m, 1H), 2.56 (s, 3H), 2.46 (s, 3H), 2.30 (dd, J=17.7 and 9.4 Hz, 1H), 1.90–1.60 (m, 4H); $^{13}$C NMR (CDC$_3$) δ 152.2, 151.5, 146.6, 134.3, 131.0, 130.0, 127.9, 123.4, 119.4, 117.1, 114.0, 113.3, 111.6, 67.0, 57.4, 40.7, 31.4, 29.5, 21.8, 21.7; FAB HRMS calculated for [$C_{20}H_{23}N_5O_2$.H] 366.1932, found 366.1957.

I. (R)-3-(N-Methylpyrrolidin-2-ylmethyl)-5-(3-nitropyrid-2-ylamino)-1H-indole (R)-3-(N-Methylpyrrolidin-2-ylmethyl)indole and 2-chloro-3-nitropyridine were used. Triethylamine was used as base, acetonitrile was used as solvent, and the reaction was heated at reflux for 3.5 hours. Chromatography afforded the title compound (81%) as a dark red foam: $^1$H NMR (CDCl$_3$) δ 10.11 (br s, 1H), 8.52 (dd, J=1.8 and 8.4 Hz, 1H), 8.43 (1.8 and 4.5 Hz, 1H), 8.33 (br s, 1H), 7.77 (d, J=1.7 Hz, 1H), 7.35 (d, J=8.7 Hz, 1H), 7.26 (dd, J=2.0 and 8.6 Hz, 1H), 7.03 (d, J=2.1 Hz, 1H) 6.74 (dd, J=4.4 and 8.4 Hz, 1H), 3.21–3.12 (m, 2H), 2.68–2.2.58 (m, 1H), 2.54–2.46 (m, 1H), 2.47 (s, 3H), 2.28–2.18 (m, 1H), 1.89–1.73 (m, 2H), 1.73–1.54 (m, 2H); $^{13}$C NMR (CDCl$_3$) δ 155.7, 151.5, 135.5, 134.3, 129.5, 128.2, 128.1, 123.1, 119.4, 114.3, 113.0, 111.4, 66.7, 57.5, 40.8, 31.5, 29.9, 21.9. Anal. calcd for $C_{19}H_{21}N_5O_2 \cdot \frac{1}{3}\ H_2O$: C, 63.85; H, 6.11; N, 19.59. Found: C, 63.86; H, 5.86; N, 19.31.

J. 5-(6-Methoxy-3-nitropyrid-2-ylamino)-3-(N-methylpyrrolidin-2-ylmethyl)-1H-indole (R)-5-Amino-3-(N-methylpyrrolidin-2-ylmethyl)-1H-indole and 2-chloro-6-methoxy-3-nitropyridine were used. Triethylamine was used as base, absolute ethanol was used as solvent, and the reaction was heated at reflux for 5.5 hours. Column chromatography afforded the title compound (54%) as a red amorphous solid: $^1$H NMR (CDCl$_3$) δ 8.80 (br s, NH), 8.37 (d, J=9.1 Hz, 1H), 7.85 (s, 1H), 7.34–7.28 (m, 2H), 7.03 (d, J=2.0 Hz, 1H), 6.14 (d, J=9.1 Hz, 1H), 3.85 (s, 3H), 3.19–3.11 (m, 2H), 2.61 (dd, J=13.8 and 9.5 Hz, 1H), 2.54–2.45 (m, 1H), 2.45 (s, 3H), 2.24 (dd, J=17.1 and 9.3 Hz, 1H), 1.91–1.54 (m, 4H); $^{13}$C NMR (CDCl$_3$) δ 166.9, 151.3, 138.2, 134.0, 129.6, 127.8, 123.3, 122.0, 118.6, 114.1, 113.3, 111.1, 102.0, 66.5, 57.5, 54.7, 40.8, 31.6, 29.9, 21.9; HRMS calculated for C$_{20}$H$_{23}$N$_5$O$_3$ 381.1803, found 381.1799.

K. 3-(N-Methylpyrrolidin-2-ylmethyl)-5-(4-trifluoromethyl-2-nitrophenylamino-1H-indole (R)-5-Amino-3-(N-methylpyrrolidin-2-ylmethyl)-1H-indole and 4-chloro-3-nitrobenzotrifluoride were used. Triethylamine was used as base, absolute ethanol was used as solvent, and the reaction was heated at reflux for 4.5 hours. Column chromatography afforded the title compound (38%) as a red foam: R$_f$=0.30 in 9:1:0.1 [methylene chloride/methanol/ammonium hydroxide]; $^{13}$C NMR (CDCl$_3$) δ 147.0, 139.7, 135.1, 131.6, 131.0, 129.2, 128.5, 124.7, 124.2, 120.7, 118.6, 116.8, 116.6, 113.6, 112.6, 67.1, 57.4, 40.8, 31.3, 29.2, 21.9. FAB LRMS 419 [MH$^+$]. Anal. calcd for C$_{21}$H$_{21}$F$_3$N$_4$O$_2$.0.6 CH$_2$Cl$_2$: C, 55.27; H, 4.77; N, 11.94. Found: C, 55.44; H, 4.58; N, 11.52.

L. 3-(2-Dimethylaminoethyl)-5-(3-nitropyrid-2-ylamino)-1H-indole

5-Amino-3-(2-dimethylaminoethyl)indole and 2-chloro-3-nitropyridine were used. Triethylamine was used as base, p-dioxane was used as solvent, and the reaction was heated at reflux (101° C.) for 3 hours. Chromatography afforded the title compound (67%) as a dark red foam: mp, 59.0°–61.0° C.; $^1$H NMR (CDCl$_3$) δ 8.66 (br s, 1H), 8.51 (dd, J=8.3 and 1.8 Hz, 1H), 8.41 (dd, J=4.4 and 1.8 Hz, 1H), 7.76 (br s, 1H), 7.30–7.24 (m, 2H), 6.97 (d, J=2.1 Hz, 1H), 6.73 (dd, J=8.3 and 4.4 Hz, 1H), 2.97–2.91 (m, 2H), 2.70–2.63 (m, 2H), 2.36 (s, 6H); $^{13}$C NMR (CDCl$_3$) δ 155.7, 151.5, 135.5, 134.5, 129.4, 128.2, 127.9, 122.8, 119.3, 114.4, 114.3, 113.0, 111.5, 60.3, 45.4, 23.7. Anal. calcd for C$_{17}$H$_{19}$N$_5$O$_2$.⅓ H$_2$O: C, 61.62; H, 5.98; N, 21.13. Found: C, 61.58; H, 5.65; N, 20.80.

M. 3-(N-Methylpyrrolidin-2-ylmethyl)-5-(4-phenyl-2-nitrophenylamino)-1H-indole (R)-5-Amino-3-(N-methylpyrrolidin-2-ylmethyl)-1H-indole and 4-bromo-3-nitrobiphenyl were used. Triethylamine was used as base, N,N-dimethylformamide was used as solvent, and the reaction was heated at 110° C. for 12 hours. Column chromatography afforded the title compound (24%) as a red amorphous solid: $^1$H NMR (CDCl$_3$) δ 9.63 (br s, NH), 8.97 (br s, NH), 8.42 (d, J=2.2 Hz, 1 H), 7.56–7.25 (m, 9H), 7.08 (d, J=9.0 Hz, 2H), 3.50–3.32 (m, 2H), 2.95–2.79 (m, 2H), 2.59–2.52 (m, 1H), 2.53 (s, 3H), 2.05–1.71 (m, 4H); $^{13}$C NMR (CDCl$_3$) δ 144.4, 138.8, 134.9, 134.5, 132.4, 131.1, 130.2, 129.7, 129.0, 127.3, 126.2, 124.7, 124.1, 120.8, 116.7, 115.9, 112.7, 112.0, 67.9, 57.4, 40.6, 31.2, 28.6, 21.9; FAB HRMS calculated for [C$_{26}$H$_{26}$N$_4$O$_2$.H] 427.2136, found 427.2099.

N. 5-(5,6-Dichloro-2-nitrophenylamino)-3-(N-methylpyrrolidin-2-ylmethyl)-1H-indole (R)-5-Amino-3-(N-methylpyrrolidin-2-ylmethyl)-1H-indole and 1,2,3-trichloronitrobenzene were used. Sodium carbonate was used as base, N,N-dimethylformamide was used as solvent, and the reaction was heated at 125° C. for 3 hours. Column chromatography afforded the title compound (60%) as a red solid: R$_f$=0.4 in 9:1:0.1 [methylene chloride/methanol/ammonium hydroxide]; $^1$H NMR (CDCl$_3$) δ 8.59 (br s, NH), 8.36 (br s, NH), 7.96 (d, J=9.1 Hz, 1H), 7.23 (d, J=8.6 Hz, 1H), 7.09 (s, 1H), 7.07 (d, J=9.1 Hz, 1H), 6.99 (d, J=1.9 Hz, 1H), 6.81 (dd, J=8.6 and 2.1 Hz, 1H), 3.15–3.05 (m, 2H), 2.54 (dd, J=13.8 and 9.6 Hz, 1H), 2.46–2.33 (m, 1H), 2.40 (s, 3H), 2.22 (dd, J=17.4 and 9.3 Hz, 1H), 1.84–1.48 (m, 4H); FAB HRMS calculated for [C$_{20}$H$_{20}$Cl$_2$N$_4$O$_2$.H] 419.1044, found 419.1046.

O. 3-(N-t-Butoxycarbonylpiperid-4-yl)-5-(3-nitropyrid-2-ylaminol-1H-indole

5-Amino-3-(N-t-butoxycarbonylpiperid-4-yl)-1H-indole and 2-chloro-3-nitropyridine were used. Triethylamine was used as base, dioxane was used as solvent, the reaction was heated at reflux (101° C.) for 5 hours. Column chromatography using ethyl acetate [30–40%] in hexanes to afford the title compound (70%) as a dark red foam: $^1$H NMR (CDCl$_3$) δ 155.8, 155.0, 151.6, 135.5, 134.6, 129.4, 126.9, 121.3, 120.8, 119.8, 114.8, 113.1, 111.5, 79.4, 44.5, 33.6, 32.8, 28.5. Anal. calcd for C$_{23}$H$_{27}$N$_5$O$_4$.¼ C$_4$H$_8$O$_2$ [ethyl acetate]: C, 62.73; H, 6.36; N, 15.24. Found: C, 62.51; H, 6.08; N, 15.21.

P. (R,S)-3-(N-Methylpyrrolidin-3-yl)-5-(3-nitropyrid-2-ylamino)-1H-indole (R,S)-3-(N-Methylpyrrolidin-3-yl)indole and 2-chloro-3-nitropyridine were used. Sodium acetate was used as base, acetic acid was used as solvent, and the reaction was heated at reflux for 4 hours. Chromatography afforded the title compound (44%) as a dark red foam: mp, 55.0°–57.0° C.; $^{13}$C NMR (CDCl$_3$) δ 155.7, 151.5, 135.5, 135.0, 129.0, 128.1, 127.1, 121.7, 119.3, 119.2, 114.7, 113.0, 111.6, 62.8, 56.2, 42.4, 35.1, 32.1; FAB LRMS (m/z, relative intensity) 306 (MH$^+$, 100), 155 (38). Anal. calcd for C$_{18}$H$_{19}$N$_5$O$_2$.0.5 C$_4$H$_4$O$_2$ [ethyl acetate]: C, 62.98; H, 6.08; N, 18.36. Found C, 62.71; H, 5.80; N, 18.51.

Q. 5-(3-Nitropyrid-2-yl)-1H-indole

5-Aminoindole and 2-chloro-3-nitropyridine were used. Triethylamine was used as base, absolute ethanol was used as solvent, and the reaction was stirred at room temperature for 4 days. The resulting reaction mixture was filtered to afford the title compound (69%) as an orange solid: mp, 162.0°–163.5° C.; $^{13}$C NMR (CDCl$_3$) δ 155.6, 150.5, 135.5, 133.5, 129.7, 127.9, 127.6, 125.9, 118.5, 115.0, 113.4, 111.2, 101.2; Anal. calcd for C$_{13}$H$_{10}$N$_4$O$_2$: C, 61.41; H, 3.96; N, 22.04. Found: C, 61.22; H, 3.80; N, 22.08.

R. 5-(4-Chloro-2-nitrophenyl)amino-3-(N-methylpyrrolidin-2R-ylmethyl)-1H-indole (R)-5-Amino-3-(N-methylpyrrolidin-2-ylmethyl)-1H-indole and 2,5-dichloronhrobenzene were used. Sodium carbonate was used as base, N,N-dimethylformamide was used as solvent, and the reaction was heated at 110° C. for 5 hours. Column chromatography using 12:1:0.4 [methylene chloride/methanol/ammonium hydroxide] afforded the title compound (35%) as a red solid: R$_f$=0.5 in 9:1:0.1 [methylene chloride/methanol/ammonium hydroxide]; $^1$H NMR (CDCl$_3$) δ 9.58 (s, 1H), 8.21 (d, J=2.5 Hz, 1H), 8.14 (br s, 1H), 7.46 (d, J=approx 2 Hz), 7.40 (d, J=8.5 Hz, 1H), 7.21 (dd, J=2.5 and 9.3 Hz, 1H), 7.11 (d, J=approx 2 Hz), 7.05 (dd, J=2.0 and 8.5 Hz, 1H), 6.98 (d, J=9.3 Hz, 1H), 3.18–3.08 (m, 2H), 2.57 (dd, J=9.5 and 14.2 Hz, 1H), 2.50–2.40 (m, 1H), 2.28–2.17 (m, 1H), 2.44 (s, 3H), 1.85–1.50 (m, 4H).

S. 5-(5-Chloro-2-nitrophenyl)amino-3-(N-methylpyrrolidin-2R-ylmethyl)-1H-indole (R)-5-Amino-3-(N-methylpyrrolidin-2-ylmethyl)-1H-indole and 2,4-dichloronitrobenzene were used. Sodium carbonate was used as base, N,N-dimethylformamide was used as solvent, and the reaction was heated at 110° C. for 5 hours. Column chromatography using 12:1:0.4 [methylene chloride/methanol/ammonium hydroxide] afforded the title compound (51%) as a red solid: R$_f$=0.5 in 9:1:0.1 [methylene chloride/methanol/ammonium hydroxide]; FAB HRMS calculated for [C$_{20}$H$_{21}$N$_4$ ClO$_2$.H] 385.1434, found 385.1451.

T. 5-(6-Chloro-2-nitrophenyl)amino-3-(N-methylpyrrolidin-2R-ylmethyl)-1H-indole (R)-5-Amino-3-(N-methylpyrrolidin-2-ylmethyl)-1H-indole and 2,3-dichloronitrobenzene were used. Sodium carbonate was used as base, N,N-dimethylformamide was used as solvent, and the reaction was heated at 110° C. for 5 hours. Column chromatography using 12:1:0.4 [methylene chloride/methanol/ammonium hydroxide] afforded the title compound (62%) as a red solid: $R_f$=0.5 in 9:1:0.1 [methylene chloride/methanol/ammonium hydroxide]; $^1$H NMR (CDCl$_3$) δ 8.33 (s, 1H), 8.21 (br s,1H), 7.99 (dd, J=1.5 and 8.5 Hz, 1H), 7.56 (dd, J=1.6 and 7.8 Hz, 1H), 7.25 (d, J=8.5 Hz, 1H), 7.08 (d J=1.8 Hz, 1H), 7.05 (d, J=2.1 Hz 1H), 6.92 (dd, J=7.8 and 8.4 Hz, 1H), 6.82 (dd, J=2.1 and 8.6 Hz, 1H), 3.22–3.10 (m, 2H), 2.65–2.50 (m, 2H), 2.41 (s, 3H), 2.29 (dd, J=17.2 and 9.4 Hz, 1H), 1.90 –1.55 (m, 4H).

U. 5-(4-Cyano-2-nitrophenyl)amino-3-(N-t-butoxycarbonyl-1,2,5,6-tetrahydropyrid-4-yl)-1H-indole 5-Amino-3-(N-t-butoxycarbonyl-1,2,5,6-tetrahydropyrid-4-yl)-1H-indole and 4-chloro-3-nitrobenzonitrile were used. Triethylamine was used as base, absolute ethanol was used as solvent, and the reaction was heated at reflux for 2 hours. Column chromatography using 1% methanol in methylene chloride afforded the title compound (40%) as a red foam: mp, decomposes 85° C.; $R_f$=0.35 in 1% methanol in methylene chloride; HRMS calculated for $C_{25}H_{25}N_5O_4$ 459.1909, found 459.1853.

V. 5-(4-Cyano-2-nitrophenyl)amino-3-(N-methylpyrrolidin-3-yl)-1H-indole

5-Amino-3-(N-methylpyrrolidin-3-yl)-1H-indole and 4-chloro-3-nitrobenzonitrile were used. Sodium acetate was used as base, acetic acid was used as solvent, and the reaction was heated at reflux for 5 hours. Column chromatography afforded the title compound (16%) as a red amorphous solid: $R_f$=0.35 in 9:1:0.1 [methylene chloride/methanol/ammonium hydroxide]; $^{13}$C NMR (CDCl$_3$) δ 147.4, 137.0, 135.8, 132.1, 131.4, 128.2, 127.8, 122.2, 120.4, 120.3, 118.2, 117.2, 117.1, 112.7, 98.9, 62.7, 56.3, 42.4, 35.0, 32.3; HRMS calculated for $C_{20}H_{19}N_5O_2$ 361.1541, found 361.1500.

W. 5-(5-Cyano-3-nitropyrid-2-yl)amino-3-(N-methylpyrrolidin-3-ylmethyl)-1H-indole (R)-5-Amino-3-(N-methylpyrrolidin-2-ylmethyl)-1H-indole and 2-chloro-5-cyano-3-nitropyridine were used. Triethylamine was used as base, absolute ethanol was used as solvent, and the reaction was heated at reflux for 2 hours. Column chromatography using 9:1:0.1 [methylene chloride/methanol/ammonium hydroxide] afforded the title compound (53%) as a red foam: $R_f$=0.2 in 20% methanol in methylene chloride; $^{13}$C NMR (CD$_3$OD) δ 158.3, 140.3, 136.5, 130.0, 128.4, 125.9, 122.2, 120.4, 115.2, 112.8, 111.1, 98.4, 70.1, 57.9, 40.4, 31.3, 28.2, 22.4; HRMS calculated for $C_{20}H_{20}N_6O_2$ 376.1650, found 376.1653.

X. 5-(4-Methyl-2-nitrophenyl)amino-3-(N-methylpyrrolidin-2R-ylmethyl )-1H-indole (R)-5-Amino-3-(N-methylpyrrolidin-2-ylmethyl)-1H-indole and 4-chloro-3-nitrotolune were used. No base was used, 4-chloro-3-nitrotolune was used as solvent, and the reaction was heated at 150° C. for 18 hours. Column chromatography using 18:1:0.1 [methylene chloride/methanol/ammonium hydroxide] afforded the title compound (63%) as a red foam: $R_f$=0.6 in 18:1:0.1 [methylene chloride/methanol/ammonium hydroxide]; $^{13}$C NMR (CD$_3$OD) δ 144.8, 138.2, 136.6, 132.9, 131.3, 129.6, 127.2, 126.3, 125.1, 121.2, 117.3, 116.8, 113.8, 113.3, 68.4, 58.3, 41.0, 32.3, 30.2, 22.4, 20.0. Anal. calcd. for $C_{21}H_{24}N_4O_2$.0.5 H$_2$O: C, 67.54; H, 6.75; 15.00. Found: C, 67.58; H, 6.90; N, 14.66.

EXAMPLE 9

General Procedure for the Conversion of 5-(2,5-Dimethyl-1H-pyrrol-1-yl)-1H-indoles to 5-Amino-1H-indoles A mixture of the 5-(2,5-dimethyl-1H-pyrrol-1-yl)-1H-indole (10.00 mmol), hydroxylamine hydrochloride (6.95 g, 100 mmol, 10 eq), and triethylamine (6.97 mL, 50.0 mmol, 5 eq) in 2-propanol (35 mL) and water (5 mL) was heated at reflux under nitrogen for a time depending on the substrate. The resulting reaction mixture was cooled, solid sodium hydroxide (4.00 g, 100 mmol, 10 eq) was added, and the resulting reaction mixture was stirred at room temperature under nitrogen for 24 hours. The reaction mixture was then filtered through Celite®, and the filtrate was evaporated under reduced pressure. The residue was column chromatographed using silica gel (approximately 100 g) and eluting with an appropriate solvent system to afford the appropriate 5amino-1H-indole.

Following this procedure the following compounds were prepared.

A. 5-Amino-3-(N-(2-methoxyethyl)pyrrolidin-2R-ylmethyl)-1H-indole 5-(2,5-Dimethyl-1H-pyrrol-1-yl)-3-(N-(2-methoxyethyl)pyrrolidin-2R-ylmethyl)-1H-indole was used, and the reaction reflux time was 4.5 hours. Chromatography using elution with 18:1:1 [ethyl acetate/methanol/triethylamine] afforded the title compound (71%) as a brown foam: $R_f$=0.70 in ethyl acetate/methanol/triethylamine [8:1:1]; $^{13}$C NMR (CD$_3$OD) δ 146.0, 138.0, 132.0, 128.2, 122.7, 112.8, 111.2, 104.4, 70.9, 65.9, 57.6, 54.6, 53.7, 30.2, 29.4, 21.4; FAB HRMS calculated for [$C_{16}H_{22}N_3O.H$] 273.1861, found 273.1838. Anal. calcd for $C_{16}H_{22}N_3O.0.9 H_2O$: C, 66.59; H, 8.31; N, 14.56. Found: C, 66.59; H, 8.15; N, 14.34.

B. 5-Amino-3-(N-benzyloxycarbonyl-4R-methoxypyrrolidin-2R-ylmethyl)-1H-indole 5-(2,5-Dimethyl-1H-pyrrol-1-yl)-3-(N-benzyloxycarbonyl-4R-methoxypyrrolidin-2R-ylmethyl)-1H-indole was used, and the reaction reflux time was 4 hours. Chromatography using elution with 18:1:1 [ethyl acetate/methanol/triethylamine] afforded the title compound (92%) as a clear, pale brown oil: $R_f$=0.80 in methylene chloride/methanol/ammonium hydroxide [6:1:0.1].

C. 5-Amino-3-(N-t-butoxycarbonylpyrrolidin-2R-ylmethyl)-1H-indole 3-(N-t-Butoxycarbonylpyrrolidin-2R-ylmethyl)-5-(2,6-dimethyl-1H-pyrrol-1-yl)-1H-indole was used, and the reaction reflux time was 12 hours. Chromatography using ethyl acetate/hexanes [1:1] afforded the title compound (78%) as a pale brown foam: mp, decomposes 50° C.; $R_f$=0.30 in ethyl acetate/hexanes (1:1); IR (KBr) 1673, 1405 cm$^{-1}$; HRMS calculated for $C_{18}H_{25}N_3O_2$ 315.1949, found 315.1914.

D. 5-Amino-3-(N-methylpyrrolidin-2R-ylmethyl)-1H-indole 5-(2,5-Dimethyl-1H-pyrrol-1-yl)-3-(N-methylpyrrolidin-2R-ylmethyl)-1H-indole was used, and the reaction reflux time was 4.5 hours. Chromatography using ethyl acetate/methanol/triethylamine [8:1:1] afforded the title compound (83%) as a brown foam: $R_f$=0.4 in ethyl acetate/methanol/triethylamine [8:1:1]; mp, 43°–47° C.; $^{13}$C NMR CDCl$_3$) δ 138.9, 131.2, 128.5, 122.7, 112.8, 112.7, 111.7, 104.0, 66.7, 57.5, 40.7, 31.5, 29.8, 21.8; HRMS calculated for $C_{14}H_{19}N_3$ 229.1581, found 229.1560.

EXAMPLE 10

General Procedure for the Conversion of 3-(N-Benzyloxycarbonylpyrrolidin-2-ylcarbonyl)-1H-indoles to 3-(N-Methylpyrrolidin-2-ylmethyl)-1H-indoles To a stirred mixture of lithium aluminum hydride (1.71 g, 45.1 mmol, 4.5 eq) in anhydrous tetrahydrofuran (40 mL) at 0° C. was added dropwise a solution of the 3-(N-benzyloxycarbonylpyrrolidin-2-ylcarbonyl)-1H-indole (10.0 mmol) in anhydrous tetrahydrofuran (20 mL). The resulting reaction mixture was heated at reflux under nitrogen for 6 hours. The reaction mixture was cooled, and sodium sulfate decahydrate (50 g) was added very carefully portionwise, followed by water (1mL), and ethyl acetate (100 mL). The resulting mixture was stirred at room temperature under nitrogen for 24 hours. The reaction mixture was then filtered through Celite®, and the filtrate was evaporated under reduced pressure. The residue was then column chromatographed using silica gel (approximately 100 g) eluting with an appropriate solvent system to afford the desired 3-(N-methylpyrrolidin-2-ylmethyl)-1H-indole.

Following this procedure the following compounds were prepared.

A. 5-(2,5-Dimethyl-1H-pyrrol-1-yl)-3-(N-methylpyrrolidin-2R-ylmethyl)-1H-indole 5-(2,5Dimethyl-1H-pyrrol-1-yl)-3-(N-benzyloxycarbonylpyrrolidin-2R-ylcarbonyl)-1H-indole was used. Chromatography using elution with ethyl acetate/methanol/triethylamine [8:1:1] afforded the title compound (92%) as a white foam: mp, 52°–58° C.; $^{13}$C NMR (CD$_3$OD) δ 137.2, 131.7, 129.9, 129.1, 125.2, 122.6, 119.0, 114.0, 112.6, 105.9, 68.5, 58.3, 41.0, 32.4, 30.2, 22.4, 13.2; [α]$^{25}$= +81° (methylene chloride, c=1). Anal. calcd for $C_{20}H_{25}N_3$.0.5 $H_2O$: C, 75.92; H, 8.28; N, 13.27. Found: C, 75.88; H, 8.43; N, 13.24.

B. (R)-5-Dibenzylamino-3-(N-methylpyrrolidin-2-ylmethyl)-1H-indole 3-(N-Benzyloxycarbonylpyrrolidin-2R-ylcarbonyl)-5-dibenzylamino-1H-indole was used. Chromatography using elution with methylene chloride/methanol/ammonium hydroxide [9:1:0.1] afforded the title compound (89%) as a pale green foam: $^1$H NMR (CDCl$_3$) δ 7.82 (br s, NH), 7.35–7.19 (m, 10 H), 7.20 (d, J=8.6 Hz, 1H), 6.95 (d, J=2.1 Hz, 1H), 6.85 (dd, J=2.3 and 8.7 Hz, 1H), 6.80 (d, J=2.2 Hz, 1H), 4.65 (s, 4H 3.25–3.02 (m, 2H), 2.52 (dd, J=9.5 and 13.9 Hz, 1H), 2.39–2.15 (m, 2 H), 2.30 s, 3H), 1.85–1.40 (m, 4H); $^{13}$C NMR (CDCl$_3$) δ 143.2, 139.7, 130.5, 128.5, 128.2, 127.3, 126.8, 122.9, 112.5, 112.2, 111.8, 103.4, 67.0, 57.4, 56.4,40.6, 31.4, 29.7, 21.9; HRMS calculated for $C_{28}H_{31}N_3$ 409.2520, found 409.2475.

EXAMPLE 11

General Procedure for the Conversion of 3-(Pyrrolidin-2-ylcarbonyl)-1H-indoles to 3-(Pyrrolidin-2-ylmethyl)-1H-indoles To a stirred solution of lithium borohydride (0.33 g, 15.2 mmol, 3.0 eq) in anhydrous tetrahydrofuran (10 mL) under nitrogen was added dropwise a solution of the 3-(pyrrolidin-2-ylcarbonyl)-1H-indole (10 mmol) in anhydrous tetrahydrofuran (40 mL). The resulting reaction solution was heated at reflux under nitrogen for a time depending on the substrate. The reaction was then cooled, and sodium sulfate decahydrate (approximately 25 g) was added slowly with caution, followed by water (1 mL), and ethyl acetate (50 mL). The resulting reaction mixture was stirred at room temperature under nitrogen for 4 hours. Then the reaction mixture was filtered through Celite®, and the filtrate was evaporated under reduced pressure. The residue was column chromatographed using silica gel (approximately 200 g) eluting with an appropriate solvent system to afford the appropriate 3-(pyrrolidin-2-ylmethyl)-1H-indole.

Following this procedure the following compounds were prepared.

A. 5-(2,5-Dimethyl-1H-pyrrol-1-yl)-3-(N-benzyloxycarbonylpyrrolidin-2R-ylmethyl)-1H-indole 5-(2,5-Dimethyl-1H-pyrrol-1-yl)-3-(N-benzyloxycarbonylpyrrolidin-2R-ylcarbonyl)-1H-indole was used, and the reaction reflux time was 1.5 hours. Chromatography using elution with ethyl acetate/hexanes [1:3] afforded the title compound (59%) as a colorless oil/foam: R$_f$=0.45 in ether; IR (KBr) 3340–3300, 1686, 1680, 1451, 1415 cm$^{-1}$; FAB LRMS (m/z, relative intensity) 428 (M$^+$, 100), 294 (14), 224 (32); FAB HRMS calculated for [$C_{27}H_{29}N_3O_2$.H] 428.2340, found 428.2303. Anal. calcd for $C_{27}H_{29}N_3O_2$.0.75 $H_2O$: C, 73.53; H, 6.97; N, 9.53. Found: C, 73.49; H, 6.71; N, 9.17.

B. 5-(2,5-Dimethyl-1H-pyrrol-1-yl)-3-(N-benzyloxycarbonyl-4R-methoxypyrrolidin-2R-ylmethyl)-1H-indole 3-(N-Benzyloxycarbonyl-4-methoxypyrrolidin-2R-ylcarbonyl)-5-(2,5-dimethyl-1H-pyrrolyl)-1H-indole was used, and the reaction reflux time was 12 hours. Chromatography using elution with 30% methylene chloride in hexanes afforded the title compound (57%) as a clear, colorless oil, which crystallized upon standing: R$_f$=0.80 in methanol/ethyl acetate [1:9]; FAB LRMS (m/z, relative intensity) 458 (MH$^+$, 100), 367 (7), 350 (5), 324 (17), 239 (10); FAB HRMS calculated for [$C_{28}H_{31}N_3O_3$.H] 458.2446, found 458.2468.

C. 3-(N-Benzyloxvcarbonylpyrrolidin-2R-ylmethyl)-5-dibenzylamino-1H-indole 3-(N-Benzyloxycarbonylpyrrolidin-2R-ylcarbonyl)-5-dibenzylamino-1H-indole was used, and the reaction reflux time was 4 hours. Chromatography using elution with ethyl acetate/hexanes [1:3] afforded the title compound (70%) as a white foam: FAB LRMS (m/z, relative intensity) 530 (MH$^+$, 87), 529 (M$^+$, 100), 439 (10), 409 (10), 325 (32), 235 (20).

EXAMPLE 12

General Method for the Formation of 3-(N-benzyloxycarbonylpyrrolidin-2-ylcarbonyl)-1H-indoles To a stirred solution of the N-benzyloxycarbonylproline (10 mmol) in anhydrous methylene chloride (25 mL) with a trace of N,N-dimethylformamide (0.1 mL) was added oxalyl chloride (1.31 mL, 15.02 mmol, 1.5 eq). The resulting effervescing reaction solution was stirred at room temperature under nitrogen for 3 hours. The reaction solution was then evaporated under reduced pressure, anhydrous hexanes (50 mL) was added, and the resulting solution was again evaporated under reduced pressure to afford the N-benzyloxycarbonylproline acid chloride which was dissolved in anhydrous benzene (25 mL).

Concomitantly, a solution of ethyl magnesium bromide (3.0M in ether, 6.8 mL, 20.4 mmol, 2.0 eq) was added dropwise to a stirred solution of a 3-unsubstituted-1H-indole (20.0 mmol, 2.0 eq) in benzene (50 mL) at 0° C. under nitrogen. The resulting reaction solution was stirred at 0° C. under nitrogen for 15 minutes. Then the solution of N-benzyloxycarbonylproline acid chloride in benzene from above was then added dropwise with vigorous stirring. The resulting reaction mixture was stirred vigorously at 0° C. under nitrogen for 1 hour. Then a saturated solution of sodium hydrogen carbonate (75 mL) was added, and this aqueous mixture was extracted with ethyl acetate (3×75 mL). The organic extracts were combined, dried (MgSO$_4$), and evaporated under reduced pressure. The residual foam was crystallized using a mixture of ethyl acetate in diethyl ether (25 mL total volume) to afford the appropriate 3-(N-benzyloxycarbonylpyrrolidin-2-ylcarbonyl)-1H-indole.

Following this procedure the following compounds were prepared.

A. 5-(2,5-Dimethyl-1H-pyrrol-1-yl)-3-(N-benzyloxycarbonylpyrrolidin-2R-ylcarbonyl)-1H-indole (R)-N-Benzyloxycarbonylproline and 5-(2,5-dimethyl-1H-pyrrol-1-yl)-1H-indole were used. Crystallization of the extraction residue using diethyl ether afforded the title compound (75%) as an off-white solid: mp, 155.0°–157.0° C. with effervescence; $[\alpha]^{25}$=+101° (methylene chloride, c=1). Anal. calcd for $C_{27}H_{27}N_3O_3$: C, 73.45; H, 6.16; N, 9.52. Found: C, 73.41; H, 6.02; N, 9.52.

B. 3-(N-Benzyloxycarbonyl-4-methoxypyrrolidin-2R-ylcarbonyl)-5-(2,5-dimethyl-1H-pyrrolyl)-1H-indole (R)-cis-N-Benzyloxycarbonyl-4-methoxyproline [Krapcho, et. al, *J. Med. Chem*, 1148 (1988)] and 5-(2,5-dimethyl-1H-pyrrol-1-yl)-1H-indole were used. Crystallization of the extraction residue using diethyl ether afforded the title compound (54%) as an off-white solid: mp 189.0°–191.0° C.; $R_f$=0.4 in ethyl acetate/hexanes [2:1]; $[\alpha]^{25}$=+89° (methylene chloride, c=1); FAB HRMS calculated for $[C_{28}H_{29}N_3O_4.H]$ 472.2238, found 472.2281. Anal. calcd for $C_{28}H_{29}H_3O_4$: C, 71.32; H, 6.20; N, 8.91. Found: C, 71.56; H, 6.28; N, 8.92.

C. 3-(N-Benzyloxycarbonylpyrrolidin-2R-ylcarbonyl)-5-dibenzylamino-1H-indole (R)-N-Benzyloxycarbonylproline and 5-dibenzylamino-1H-indole were used. Crystallization of the extraction residue using diethyl ether afforded the title compound (24%) as a white solid: mp, 176.0°–177.0° C.; LRMS (m/z, relative intensity) 543 (100, $M^+$), 453 (10), 407 (7), 339 (40), 307 (10), 247 (10), 154 (38); $[\alpha]^{25}$=+112° (THF, c=1); Anal. calcd for $C_{35}H_{33}N_3O_3$: C, 77.32; H, 6.12; N, 7.73. Found: C, 77.35; H, 6.30; N, 7.66.

EXAMPLE 13

(R)-5-Amino-3-(N-methylpyrrolidin-2-ylmethyl)-1H-indole

A mixture of (R)-5-dibenzylamino-3-(N-methylpyrrolidin-2-ylmethyl)-1H-indole (1.08 g, 2.64 mmol) and 20% palladium hydroxide on carbon (0.6 g) in absolute ethanol (25 mL) was shaken under a hydrogen atmosphere (3 atm) at 40 °C. for 4 hours. The resulting mixture was filtered through diatomaceous earth, and the filtrate was evaporated under reduced pressure to afford the title compound (0.60 g, 2.62 mmol, 99%) as a white foam: $^1$H NMR (DMSO-$d_6$) δ 10.65 (br s, NH), 7.14 (d, J=2.2 Hz, 1H), 7.12 (d, J=8.6 Hz, 1H), 6.85 (d, J=1.6 Hz, 1H), 6.60 (dd, J=2.0 and 8.6 Hz, 1H), 3.63–2.83 (m, 7H), 2.78 (s, 3H), 2.05–1.67 (m, 4H); $[\alpha]^{25}$=+9° (MeOH, c=1.0); HRMS calculated for $C_{14}H_{19}N_3$: 229.1575; found: 229.1593.

EXAMPLE 14

5-(2,5-Dimethyl-1H-pyrrol-1-yl)-1H-indole

A mixture of 5-aminoindole (1.32 g, 10.0 mmol), acetonylacetone (4.0 mL, 34 mmol, 3.4 eq) and toluene (25 mL) was heated at reflux under nitrogen using a Dean-Stark trap for 24 hours. The reaction was cooled and then poured through a silica gel (approximately 200 g) filter followed by 10% ether in hexanes to afford the title compound (1.52 g, 72%) as an off-white, crystalline solid: $R_f$=0.75 in diethyl ether; $^{13}$C NMR (CDCl$_3$) δ 135.0, 131.4, 129.5, 128.1, 125.6, 122.4, 120.3, 111.3, 105.0, 103.0, 13.2. Anal. calcd for $C_{14}H_{14}N_2$; C, 79.97; H, 6.71; N, 13.32. Found: C, 79.72; H, 6.75; N, 13.13.

EXAMPLE 15

5-Dibenzylamino-1H-indole

To a stirred mixture of 5-aminoindole (3.00 g, 22.7 mmol) and triethylamine (10.5 mL, 74.9 mmol, 3.3 eq) in acetonitrile (30 mL) at room temperature under nitrogen was added benzyl bromide (8.2 mL, 68.9 mmol, 3.0 eq) dropwise. The resulting reaction mixture was heated at reflux under nitrogen for 3 hours. The resulting reaction mixture was filtered, and the filtrate was evaporated under reduced pressure. Column chromatography of the residue using silica gel (approximately 200 g) and elution with ethyl acetate/hexanes [1:9 to 1:1] afforded the title compound as an off white solid: mp, 124.0°–126.0° C.; $^{13}$C NMR (acetone-$d_6$) δ 144.3, 140.8, 131.8, 129.9, 129.2, 128.3, 127.5, 125.7, 113.5, 112.4, 106.4, 101.9, 57.0; TLC [15% ethyl acetate in hexanes]: $R_f$=0.3.

EXAMPLE 16

5-Amino-3-(N-methylpyrrolidin-3-yl)-1H-indole

A mixture of 5-benzylamino-3-(N-methylpyrrolidin-3-yl)-1H-indole (7.80 g, 25.5 mmol), ammonium formate (16.10 g, 255 mmol, 10 eq), and 10% Pd on carbon (0.78 g) in absolute ethanol (250 mL) was heated at reflux under nitrogen for 1 hour. Reaction filtered, and filtrate evaporated under reduced pressure. The residual oil was column chromatographed using silica gel (approximately 200 g) and elution with 0.3% triethylamine in methanol to afford the title compound (0.90 g, 16%) as a pale yellow oil: $^1$H NMR (CD$_3$OD) δ 7.13 (d, J=8.5 Hz, 1H), 6.94 (br s, 2H), 6.65 (dd, J=2.0 and 8.5 Hz, 1H), 4.91 (s, 2-NH), 3.66–3.50 (m, 1H), 3.17–3.08 (br t, 1H), 2.96–2.85 (m, 1H); 2.67–2.50 (m, 2H), 2.40 (s, 3H), 2.37–2.24 (m, 1H), 2.08–1.93 (m, 1H); FAB LRMS (m/z, relative intensity) 216 (MH$^+$, 100).

EXAMPLE 17

5-Benzylamino-3-(N-methylpyrrolidin-3-yl)-1H-indole

To a stirred solution of N-methyl-3-(5-phenylcarbonylaminoindol-3-yl)succinamide (18.31 g, 52.71 mmol) in anhydrous tetrahydrofuran (270 mL) at 0° C. was added lithium aluminum hydride (20.01 g, 527 mmol, 10 eq) as a solid portionwise over 45 minutes. The resulting reaction mixture was stirred at room temperature under nitrogen for 24 hours. Sodium sulfate decahydrate (50 g) was then carefully added to the reaction mixture followed by water (5 mL) and ethyl acetate (100 mL). The resulting mixture was stirred at room temperature for 1 hour. The reaction mixture was filtered, and the filtrate was evaporated under reduced pressure. The residual oil was column chromatographed using silica gel (approximately 500 g) and elution with ethyl acetate: methanol: triethylamine [9:0:1 to 8:1:1] to afford the title compound (7.90 g, 49%) as a pale yellow oil: $^{13}$C NMR (acetone-$d_6$) δ 142.9, 142.1, 132.3, 129.3, 128.6, 127.5, 121.9, 118.6, 112.8, 112.5, 102.0, 63.6, 57.1, 49.9, 42.8, 36.5, 33.0; FAB LRMS (m/z, relative intensity) 306 (MH$^+$, 100), 263 (4), 248 (4), 223 (8).

EXAMPLE 18

N-Methyl-3-(5-phenylcarbonylaminoindol-3-yl)succinamide

A solution of 5-phenylcarbonylamino-1H-indole (2.50 g, 10.58 mmol) [Chem. Abstracts, 10991 g (1954)] and N-methylmaleimide (2.94 g, 26.46 mmol, 2.5 eq) in glacial acetic acid (75 mL) was heated at reflux under nitrogen for 24 hours. The resulting reaction solution was evaporated under reduced pressure, and the residual oil was dissolved in ethyl acetate (50 mL). This solution was washed with a saturated solution of sodium hydrogen carbonate (2×25 mL), dried ($MgSO_4$), and evaporated under reduced pressure. The residual oil was column chromatographed using silica gel (approximately 100 g) and elution with ethyl acetate: hexanes [1:3 to 1:1] to afford the title compound (1.06 g, 29%) as a white solid: mp, 226.5°–227.5° C.; FAB LRMS (m/z, relative intensity) 348 ($MH^+$, 100), 332 (2), 275 (4), 263 (5). Anal. calcd for $C_{20}H_{17}N_3O_3 \cdot \frac{1}{8} H_2O$: C, 68.71; H, 4.97; N, 12.02. Found: C, 68.68; H, 4.74; N, 11.91.

EXAMPLE 19

5-Amino-3-(2-dimethylaminoethyl)indole

A mixture of 3-(2-dimethylaminoethyl)-5-nitroindole (1.85 g, 7.93 mmol) and 10% palladium on carbon (0.40 g, 20% by weight) in absolute ethanol (30 mL) was shaken under a hydrogen atmosphere (3 atm) for 6 hours. The resulting mixture was filtered through Celite®, and the Celite® pad was washed generously with absolute ethanol. The combined filtrates were evaporated under reduced pressure to afford the title compound (1.60 g, 7.87 mmol, 99%) as a clear, slightly dark, hygroscopic oil: IR ($CHCl_3$) 3480, 1610, 1585, 1460, 1335 $cm^{-1}$; $^1H$ NMR ($CDCl_3$) δ 8.10 (br m, NH), 7.12 (d, J=8.5 Hz, 1H), 6.91 (d, J=2.3 Hz, 1H), 6.88 (d, J=2.2 Hz, 1H), 6.64 (dd, j=2.2 and 8.5 Hz, 1H), 2.89–2.84 (m, 2H), 2.64–2.58 (m, 2H), 2.34 (s, 6H); $^{13}C$ NMR ($CDCl_3$) δ 139.1, 131.2, 128.3, 122.2, 113.1, 112.9, 111.7, 103.8, 60.3, 45.4, 23.7; LRMS (m/z, relative intensity) 203 (9, $M^+$), 158 (2), 145 (6), 83 (66), 58 (100). HRMS calculated for $C_{12}H_{17}N_3$ 203.1424, found 203.1418. Anal. calcd for $C_{12}H_{17}N_3 \cdot \frac{1}{2} H_2O$: C, 67.89; H, 8.55; N, 19.79. Found: C, 67.71; H, 8.60; N, 19.41.

EXAMPLE 20

3-(2-Dimethylaminoethyl)-5-nitroindole

To a stirred solution of 5-nitroindole-3-N,N-dimethylglyoxamide (5.36 g, 20.52 mmol) in anhydrous tetrahydrofuran (55 mL) was added borane in tetrahydrofuran (1.0M, 78.8 mL, 78.8 mmol, 3.8 eq) dropwise slowly. The resulting reaction solution was stirred at room temperature under nitrogen for 16 hours. A saturated solution of sodium hydrogen carbonate (200 mL) was added carefully to the reaction solution, and the resulting aqueous mixture was extracted with diethyl ether (3×150 mL). The ether extracts were combined, dried ($MgSO_4$), and evaporated under reduced pressure to afford 3-(2-dimethylaminoethyl) -5-nitroindole borane complex as a amorphous orange solid (6.9 g): $^1H$ NMR (DMSO-$d_6$) δ 11.7 (br m, NH), 8.58 (d, J=2.2 Hz, 1H), 8.00 (dd, J=2.3 and 9.0 Hz, 1H), 7.52 (d, J=8.8 Hz, 1H), 7.49 (br s, 1H), 3.23–3.17 (m, 2H), 3.02–2.97 (m, 2H), 2.63 (s, 6H). This solid was placed in absolute ethanol (150 mL) along with cesium fluoride (6.9 g) and sodium carbonate (6.9 g), and the resulting mixture was heated at reflux under nitrogen for 16 hours. The resulting reaction mixture was filtered through Celite®, and the filtrate was evaporated under reduced pressure. The residual oil was chromatographed using silica gel (approx 450 g) and elution with methylene chloride/methanol/ammonium hydroxide (8:2:0.1) to afford the title compound (2.58 g, 11.06 mmol, 54%) as a yellow solid: mp, 133.0°–135.0° C.; IR (KBr) 1625, 1575, 1550, 1520, 1480, 1470, 1460, 1445, 1380, 1370, 1330 $cm^{-1}$; $^1H$ NMR (DMSO-$d_6$) δ 11.55 (br m, NH), 8.48 (d, J=2.2 Hz, 1H), 7.94 (dd, J=2.3 and 9.0 Hz, 1H), 7.47 (d, J=9.0 Hz, 1H), 7.40 (br s, 1H), 2.88–2.83 (m, 2H), 2.53–2.48 (m, 2H), 2.19 (s, 6H); $^{13}C$ NMR (DMSO-$d_6$) δ 140.2, 139.3, 126.6, 126.5, 116.3, 116.0, 115.6, 111.7, 59.8, 45.1, 22.7; LRMS (m/z, relative intensity) 233 (7, $M^+$), 189 (7), 188 (8), 143 (10), 129 (23), 115 (14), 59 (36), 58 (100). HRMS calculated for $C_{12}H_{15}N_3O_2$ 233.1166, found 233.1155. Anal. calcd for $C_{12}H_{15}N_3O_2$: C, 61.79; H, 6.48; N, 18.01. Found: C, 61.39; H, 6.45; N, 17.68.

EXAMPLE 21

5-Nitroindole-3-N,N-dimethylglyoxamide

To a stirred mixture of 5-nitroindole (10.00 g, 61.7 mmol) and phthalimide (4.00 g, 40% by weight) in anhydrous ether (250 mL) was added oxalyl chloride (17.0 mL, 0.194 mol, 3.1 eq) dropwise. The resultant reaction mixture was stirred at room temperature under nitrogen for 72 hours. The resulting reaction mixture was chilled in an ice bath (0° C.), and a solution of ether (80 mL) and dimethylamine (80 mL, condensed at −78° C.) was added cautiously with vigorous stirring to the reaction mixture. The resulting mixture was stirred vigorously at room temperature for 1 hours. Ether was then removed from the reaction mixture via evaporation under reduced pressure, and the residue was partitioned between water (500 mL) and methylene chloride (500 mL). The pH of the aqueous layer was adjusted to pH 3 using concentrated HCl. The methylene chloride layer was removed, and the aqueous layer was extracted with methylene chloride (3×500 mL). The methylene chloride extracts were combined, dried ($MgSO_4$), and evaporated under reduced pressure. Recrystallization of the residual solid in refluxing methanol with cooling afforded the title compound ($R_f$=0.15 in 10% acetone in methylene chloride, 5.74 g, 22.0 mmol, 36%) as a pale yellow solid: mp, 248.0°–249.0° C.; IR (KBr) 1755, 1740, 1730, 1650, 1620, 1585, 1530 $cm^{-1}$; $^1H$ NMR (DMSO-$d_6$) δ 12.9 (br s, NH), 8.97 (d, J=2.3 Hz, 1H), 8.43 (s, 1H), 8.18 (dd, J=2.3 and 9.0 Hz, 1H), 7.74 (d, J=9.0 Hz, 1H), 3.02 (s, 3H), 2.95 (s, 3H); $^{13}C$ NMR (DMSO-$d_6$) δ 166.6, 143.2, 140.4, 140.2, 124.5, 118.9, 117.2, 114.2, 113.6, 36.8, 33.6; LRMS (m/z, relative intensity) 261 (24, $M^+$), 190 (29), 189 (100), 173 (15), 143 (83), 115 (23). HRMS calculated for $C_{12}H_{11}N_3O_4$ 261.0750, found 261.0746. Anal calcd for $C_{12}H_{11}N_3O_4$: C, 55.17; H, 4.24; N, 16.08. Found: C, 55.15; H, 3.96; N, 15.96.

EXAMPLE 22

5-Amino-3-(N-t-butoxycarbonylpiperid-4-yl)-1H-indole

A mixture of 3-(N-t-butoxycarbonyl-1,2,5,6-tetrahydropyrid-4-yl)-5-nitro-1H-indole (3.55 g, 10.34 mmol) and 10% palladium on carbon (0.55 g) in absolute ethanol (60 mL) was shaken under a hydrogen atmosphere (3 atm) for 7 hours at room temperature. The resulting reaction mixture was filtered through diatomaceous earth, and the filtrate was evaporated under reduced pressure. The residual solid was triturated in diethyl ether to afford the title compound (2.56 g, 78%) as a pale pink solid: mp, decomposes 215° C.; $^{13}C$ NMR ($CDCl_3$) δ 155.0, 139.0, 131.3, 127.3, 120.4, 119.8, 112.9, 111.8, 104.1, 79.4, 44.5, 33.8, 32.7, 28.5. Anal. calcd for $C_{18}H_{25}N_3O_2 \cdot \frac{1}{4} H_2O$: C, 67.57; H, 8.03; N, 13.13. Found: C, 67.20; H, 8.07; N, 13.44.

EXAMPLE 23

3-(N-t-Butoxycarbonyl-1,2,5,6-tetrahydropyrid-4-yl) -5-nitro-1H-indole

To a stirred solution of sodium (2.51 g, 105 mmol, 7 eq) in absolute methanol (50 mL) was added 5-nitroindole (2.43 g, 15.0 mmol) and N-t-butoxycarbonyl4-piperidone (8.96 g, 45.0 mmol, 3.0 eq). The resulting reaction solution was heated at reflux (65° C.) under nitrogen for 24 hours. The resulting reaction solution was evaporated under reduced pressure, and the residue was partitioned between a saturated solution of sodium hydrogen carbonate (50 mL) and ethyl acetate (50 mL). The organic layer was removed, and the aqueous layer was extracted with ethyl acetate (2×50 mL). The organic extracts were combined, dried ($MgSO_4$), and evaporated under reduced pressure. Column chromatography of the extraction residue using silica gel (approximately 100 g) and elution with ethyl acetate in hexanes [1:2 to 1:1 gradient] afforded the title compound (72%) as yellow solid: mp, decomposes 230° C.; $^1$H NMR ($CDCl_3$) δ 9.24 (br s, 1H), 8.78 (d, J=1.3 Hz, 1H), 8.09 (dd, J=1.4 and 9.4 Hz, 1H), 7.40 (d, J=9.3 Hz, 1H), 7.30 (d, J=1.8 Hz, 1H), 6.17–6.15 (m, 1H), 4.16–4.13 (m, 2H), 3.68 (t, J=5.8 Hz, 2H), 2.58–2.48 (m, 2H), 1.50 (s, 9H); Anal. calcd for $C_{15}H_{21}N_3O_4$.0.1 $H_2O$: C, 62.63; H, 6.19; N, 12.17. Found: C, 62.71; H, 6.09; N, 11.81.

EXAMPLE 24

3-(N-t-Butoxycarbonylpyrrolidin-2R-ylmethyl)-5-(2, 5-dimethyl-1H-pyrrol-1-yl)-1H-indole A mixture of 3-(N-benzyloxycarbonyl-4-methoxypyrrolidin-2R-ylcarbonyl)-5-(2,5-dimethyl-1H-pyrrolyl)-1H-indole (6.16 g, 14.41 mmol) and 10% palladium on carbon (3.32 g) in absolute ethanol (75 mL) was shaken under a hydrogen atmosphere for 20 hours at room temperature. The resulting reaction mixture was filtered through Celite®, and the filtrate was evaporated under reduced pressure. The residual foam (6.3 9) was dissolved in anhydrous tetrahydrofuran (50 mL), and di-tert-butyl dicarbonate (3.45 g, 15.85 mmol, 1.1 eq) was added dropwise to this stirred solution at room temperature. This reaction solution was stirred at room temperature under nitrogen for 30 minutes, and then the solution was evaporated under reduced pressure. The residue was column chromatographed using silica gel (approximately 200 g) eluting with ethyl acetate/hexanes [1:2] to afford the title compound (91%) as a white solid: $[\alpha]^{25}$=−1.30° (methylene chloride, c=1); HRMS calculated for $C_{24}H_{31}N_3O_2$ 393.2418, found 393.2461. Anal. calcd for $C_{24}H_{31}N_3O_2$: C, 73.25; H, 7.94; N, 10.68. Found: 73.28; H, 7.76; N, 10.51.

EXAMPLE 25

5-(3-Formylindol-5-yl)-1H-benzimidazole

A mixture of 5amino-3-(N-methylpyrrolidin-2R-ylmethyl)-1H-indole (5.50 g, 21.63 mmol) and 10% palladium on carbon (1.00 g) in absolute ethanol (75 mL) was shaken under a hydrogen atmosphere (3 atm) for 5 hours. The resulting reaction mixture was filtered through Celite®, and the filtrate was evaporated under reduced pressure. The residue (4.95 g) was dissolved in dimethylformamide dimethylacetal (25 mL), and the resulting solution was heated at reflux under nitrogen for 12 hours. The reaction solution was then evaporated under reduced pressure, and the residue was placed in a solution (75 mL) of 10% aqueous sodium hydroxide/ethanol [5:1]. The resulting mixture was heated at reflux under nitrogen for 3 hours. Concentrated hydrochloric acid was then added to this mixture to adjust the to pH 3, and this aqueous mixture was extracted with ethyl acetate (3×75 mL). The organic extracts were combined, dried ($MgSO_4$), and concentrated to approximately 20 mL volume. The precipitated solid was filtered to afford the title compound (1.54 g, 29%) as a white solid: mp >280° C.; $^1$H NMR (DMSO-$d_6$) δ 12.4 (br s, NH), 9.99 (s, CHO), 8.86 (s, 1H), 8.51–8.50 (m, 1H), 8.44–8.41 (m, 2H), 8.22 (dd, J=1.5 and 8.0 Hz, 1H), 7.76–7.67 (m, 2H), 7.39 (dd, J=4.7 and 8.0 Hz, 1H); Anal. calcd for $C_{14}H_{10}N_4$.0.25 $H_2O$: C, 67.54; H, 3.97; N, 21.00. Found: C, 67.82; H, 3.99; N, 20.68.

EXAMPLE 26

5-[3-(2-Nitroethenyl)indol-5-yl]-1H-benzimidazole

A mixture of 5-(3-formylindol-5-yl)-1H-benzimidazole (0.40 g, 1.53 mmol) and ammonium acetate (50 mg) in a solution of nitromethane (10 mL), N,N-dimethylformamide (5 mL), and dimethyl sulfoxide (1 mL) was heated at reflux under nitrogen for 4 hours. The resulting reaction mixture was cooled to room temperature and filtered to afford the title compound (0.40 g, 86%) as a yellow solid: mp >280° C.; $^{13}$C NMR (DMSO-$d_6$) δ 146.9, 145.3, 144.3, 137.4, 136.6, 135.5, 134.2, 132.1, 129.8, 127.8, 125.0, 119.9, 118.7, 115.9, 113.4, 108.7. Anal. calcd for $C_{16}H_{11}N_5O_2$.0.125 $H_2O$: C, 62.49; H, 3.69; N, 22.77. Found: C, 62.34; H, 3.51; N, 22.45.

EXAMPLE 27

5-(3-Nitropyrid-2-ylamino)-3-(N-(2,2,2-trichloroethoxycarbonyl)pyrrolidin-2R-ylmethyl)-1H-indole To a stirred solution of (R)-5-(3-nitropyrid-2-ylamino)-3-(pyrrolidin-2-ylmethyl)-1H-indole (0.42 g, 1.24 mmol) and pyridine (0.11 mL, 1.36 mmol, 1.1 eq) in anhydrous dichloroethane (6 mL) at room temperature was added 2,2,2-trichloroethyl chloroformate (0.18 mL, 1.30 mmol, 1.05 eq). The resulting reaction solution was stirred at room temperature under nitrogen for 1.5 hours. Methylene chloride was added to the resulting reaction solution, and this mixture was washed with a saturated solution of sodium hydrogen bicarbonate (20 mL). The organic layer was dried ($MgSO_4$) and evaporated under reduced pressure to afford the title compound (0.62 g, 100%) as a red amorphous solid: FAB LRMS (m/z, relative intensity) 516 ([$MH^+$ with two $^{37}$Cl and one $^{35}$Cl, 36), 515 (41), 514 ([$MH^+$ with one $^{37}$Cl and two $^{35}$Cl, 100), 513 (66), 512 ([$MH^+$ with three $^{35}$Cl], 99), 511 (36), 498 (7), 478 (14), 391 (8).

EXAMPLE 28

5-Aminomethyl-1-[3-(N-(2-methoxyethyl) pyrrolidin-2R-ylmethyl)indol-5-yl]-1H-benzimidazole To a stirred mixture of lithium aluminum hydride (0.200 g, 5.27 mmol, 3.0 eq) in anhydrous tetrahydrofuran (9 mL) was added 5-cyano-1-[3-(N-(2-methoxyethyl) pyrrolidin-2R-ylmethyl)indol-5-yl ]-1H-benzimidazole (0.700 g, 1.75 mmol), and the resultant reaction mixture was heated at reflux under nitrogen for 24 hours. Sodium sulfate decahydrate (approximately 10 grams) was then added carefully, followed by water (2 mL), and then ethyl acetate (20 mL). The resultant mixture was then stirred at room temperature for 1 hour. The mixture was filtered through Celite®, and the filtrate was evaporated under reduced pressure. The residue was column chromatographed using silica gel (approximately 50 g) and elution with 18:1:1 [ethyl acetate/methanol/triethylamine] to afford the title compound (0.358 g, 51%) as a pale yellow foam: $R_f$=0.15 in 9:1:0.1 [methylene chloride/methanol/ammonium hydroxide]; $^{13}$C NMR (CD$_3$OD) δ 145.2, 144.3, 137.6, 137.2, 135.2, 129.6, 128.7, 126.2, 125.0, 119.3, 119.1, 115.9, 114.5, 113.5, 112.1, 72.3, 67.1, 58.9, 55.8, 55.0, 46.6, 31.6, 30.5, 22.9; [α]$^{25}$=+61° (methylene chloride, c=1). Anal. calcd for C$_{24}$H$_{29}$N$_5$O.0.25 ethyl acetate [C$_4$H$_8$O$_2$].0.8 H$_2$O: C, 68.30; H, 7.47; N, 15.93. Found: C, 67.97; H, 7.19; N, 15.95.

EXAMPLE 29

5-Aminomethyl-1-[3-(N-methylpyrrolidin-2R-ylmethyl)indol-5-yl]-1H-benzimidazole A mixture of Raney nickel (approximately 0.25 g) and 5-cyano-1-[3-(N-methylpyrrolidin-2R-ylmethyl)indol-5-yl]-1H-benzimidazole (1.00 g, 2.81 mmol) in absolute ethanol saturated with ammonia was shaken under a hydrogen atmosphere (3 atm) for 5 hours. The resultant mixture was filtered through Celite®, and the filtrate was evaporated under reduced pressure to afford the title compound (0.900 g, 89%) as an off-white foam: R$_f$=0.2 in 6:2:2 [ethyl acetate/methanol/triethylamine]; $^{13}$C NMR (CD$_3$OD) δ 143.5, 142.9, 137.5, 136.1, 136.0, 133.5, 128.1, 127.4, 124.7, 123.4, 117.7, 117.5, 114.2, 113.0, 112.1, 110.5, 66.9, 56.9, 45.6, 39.6, 30.9, 28.8, 21.0; Anal. calcd for C$_{22}$H$_{25}$N$_5$.1.5 H$_2$O: C, 68.36; H, 7.30; N, 18.12. Found: C, 68.26; H, 7.38; N, 17.88.

EXAMPLE 30

General Procedure for the Acylation of 5-Aminomethyl-1-[3-(N-(2-methoxyethyl) pyrrolidin-2R-ylmethyl)indol-5-yl]-1H-benzimidazole To a stirred solution of 5-aminomethyl-1-[3-(N-(2-methoxyethyl)pyrrolidin-2R-ylmethyl) indol-5-yl]-1H-benzimidazole (0.100 g, 0.25 mmol) and triethylamine (0.04 mL, 0.3 mol, 1.1 eq) in absolute ethanol (3 mL) at room temperature was added dropwise the appropriate acylating agent (0.27 mmol, 1.1 eq). The resultant reaction solution was stirred at room temperature under nitrogen overnight, and then it was evaporated under reduced pressure. The residue was column chromatographed using silica gel (approximately 10 g) and elution with the appropriate solvent system to afford the appropriate 5-acylaminomethyl-1-[3-(N-(2-methoxyethyl)pyrrolidin-2R-ylmethyl)indol-5-yl]-1H-benzimidazole.

Following this procedure the following compounds were prepared.

A. 5-Acetylaminomethyl-1-[3-(N-(2-methoxyethyl)pyrrolidin-2R-ylmethyl)indol-5-yl]-1H-benzimidazole The acylating agent was acetyl chloride, and the reaction residue was chromatographed using elution with 5% methanol in methylene chloride to afford the title compound (68%) as a pale brown solid: R$_f$=0.35 in 10% methanol in methylene chloride; $^{13}$C NMR (CD$_3$OD) δ 173.6, 142.5, 140.6, 138.5, 132.8, 132.4, 128.8, 128.3, 128.2, 126.6, 119.4, 117.0, 114.7, 114.5, 114.4, 111.7, 70.3, 68.2, 59.3, 56.3, 55.4, 43.9, 30.9, 27.8, 22.8, 22.7; HRMS calculated for C$_{26}$H$_{31}$N$_5$O$_2$ 445.2480, found 445.2439; [α]$^{25}$=+71° (methylene chloride, c=1).

B. N-Phenyl-N'-[3-(N-(2-methoxyethyl)pyrrolidin-2R-ylmethyl)indol-5-yl]-1H-benz[b]imidazyl]methylurea The acylating agent was phenyl isocyanate, and the reaction residue was chromatographed using elution with 36:1:1 [ethyl acetate/methanol/triethylamine] to afford the title compound (57%) as an amorphous white solid: R$_f$=0.3 in 18:1:1 [ethyl acetate/methanol/triethylamine]; FAB HRMS calculated [C$_{31}$H$_{34}$N$_6$O$_2$.H] 523.2825, found 523.2866; [α]$^{25}$=+69° (methylene chloride, c=1).

C. 5-Benzoylaminomethyl-1-[3-(N-(2-methoxyethyl)pyrrolidin-2R-ylmethyl)indol-5-yl]-1H-benzimidazole The acylating agent was benzoyl chloride, and the reaction residue was chromatographed using elution with 18:1:1 [ethyl acetate/methanol/triethylamine] to afford the title compound (20%) as an amorphous white solid: R$_f$=0.5 in 18:1:1 [ethyl acetate/methanol/triethylamine]; FAB HRMS calculated [C$_{31}$H$_{33}$N$_5$O$_2$.H] 508.2715, found 508.2722; [α]$^{25}$=+75° (methylene chloride, c=1).

EXAMPLE 31

5-Amino-3-(N-t-butoxycarbonyl-1,2,5,6-tetrahydropyrid-4-yl)-1H-indole

To a stirred solution of sodium (2.61 g, 0.114 mol) in absolute methanol (50 mL) was added 5-aminoindole (2.50 g, 18.9 mmol) and 4-N-t-butoxycarbonylpiperidone (9.42 g, 47.3 mmol, 2.5 eq). The resultant reaction solution was heated at reflux under nitrogen for 6 hours. The reaction solution was then evaporated under reduced pressure, and the residue was partitioned between ethyl acetate and a solution of saturated sodium hydrogen carbonate (100 mL each). The organic layer was removed, and the aqueous layer was extracted with ethyl acetate (2×100 mL). The organic extracts were combined, dried (MgSO$_4$), and evaporated under reduced pressure. The residue was column chromatographed using silica gel (150 g) and elution with diethyl ether to afford the title compound (4.10 g, 70%) as an off-white foam: R$_f$=0.1 in diethyl ether; $^1$H NMR (CD$_3$OD) δ 7.26 (d, J=1.8 Hz, 1H), 7.17 (s, 1H), 7.16 (d, J=8.8 Hz, 1H), 6.70 (dd, J=2.0 and 8.5 Hz, 1H), 6.06 (br m, 1H), 4.88 (exchangeable H), 4.09 (br m, 2H), 3.65 (br t, J=5.7 Hz, 2H), 2.52 (br m, 2H), 1.49 (s, 9H).

EXAMPLE 32

6-Hydroxy-5-nitronicotinic Acid

A mixture of 6-hydroxynicotinic acid (16.60 g, 0.119 mol) and fuming nitric acid (166 mL) was heated at 50° C. for 4 hours. The resulting reaction solution was cooled to room temperature, and then carefully added to ice (300 g). The resultant mixture was then stored at 10° C. overnight, and the precipitated solid was filtered and dried in vacu to afford the title compound (5.50 g, 0.027 mol, 23%) as a yellow solid: $^1$H NMR (DMSO-d$_6$) δ 13.4 (br s, 2H), 8.64 (d, J=2.2 Hz, 1H), 8.37 (d, J=2.2 Hz, 1H); $^{13}$C NMR (DMSO-d$_6$) δ 164.1, 154.4, 146.1, 138.5, 137.2, 107.9. HRMS calculated for C$_6$H$_4$N$_2$O$_5$ 184.0120, found 184.0134. Anal. calcd for C$_6$H$_4$N$_2$O$_5$: C, 39.14; H, 2.19; N, 15.21. Found: C, 39.21; H, 2.33; N, 15.56.

EXAMPLE 33

6-Chloro-5-nitronicotinamide

A mixture of 6hydroxy-5-nitronicotinic acid (1.33 g, 7.22 mmol), phosphorus pentachloride (1.5 g, 7.20 mmol, 1.0 eq), and phosphorus oxychloride (2.7 mL) was heated at 130° C. under nitrogen for 4 hours. The resultant solution was concentrated via evaporation under reduced pressure. The residual oil [presumed to be 6-chloro-5-nitronicotinic acid, acid chloride] was dissolved in a solution of tetrahydrofuran and methylene chloride (1:1, 20 mL), and this solution was cooled to −78° C. A solution of ammonia in THF (2.7M, 15 mL, 40 mmol, 5 eq) was added dropwise, and the resultant reaction solution was allowed to warm to room temperature. Water (50 mL) was then added, and the aqueous mixture was extracted with methylene chloride (2×50 mL). The extracts were combined, dried (Na$_2$SO$_4$), and evaporated under reduced pressure to afford the title compound (0.72 g, 3.57 mmol, 49%) as a yellow solid: $^1$H NMR (CD$_3$OD) δ 9.05 (d, J=2.2 Hz, 1H), 8.81 (d, J=2.2 Hz, 1H), 4.88 (s, 2 exchangeable H); $^{13}$C NMR (CD$_3$OD) δ 166.7, 152.5, 146.1, 135.0, 131.3; HRMS calculated for C$_6$H$_4$ClN$_3$O$_3$ 200.9942, found 200.9938. Anal. calcd for C$_6$H$_4$ClN$_3$O$_3$; C, 35.75; H, 2.00; N, 20.85. Found: C, 35.41; H. 2.14; N, 20.29.

EXAMPLE 34

2-Chloro-5-cyano-3-nitropyrldine

A mixture of 6-chloro-5-nitronicotinamide (0.60 g, 2.98 mmol) and phosphorus oxychloride (9 mL) was heated at reflux under nitrogen for 3 hours. The reaction solution was then evaporated under reduced pressure, and the residual oil was partitioned between a saturated solution of sodium hydrogen carbonate and ethyl acetate (10 mL each). The organic layer was removed, dried (Na$_2$SO$_4$), and evaporated under reduced pressure to afford the title compound (0.38 g, 2.07 mmol, 69%) as a yellow solid: $^1$H NMR (CD$_3$OD) δ 9.00 (d, J=2.0 Hz, 1H), 8.91 (d, J=1.9 Hz, 1H); $^{13}$C NMR (CD$_3$OD) δ 156.1, 147.7, 139.4, 115.3, 111.3; HRMS calculated for C$_6$H$_2$ClN$_3$O$_2$ 182.9837, found 182.9834. Anal. calcd for C$_6$H$_2$ClN$_3$O$_2$·0.08 C$_4$H$_8$O$_2$ [ethyl acetate]: C, 39.82; H, 1.40; N, 22.05. Found: C, 39.47; H, 1.48; N, 21.99.

I claim:

1. A compound or pharmaceutically acceptable salt therof of the formula

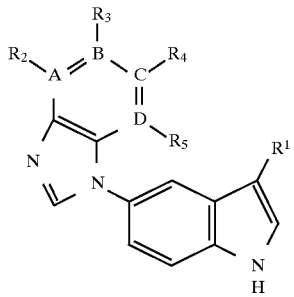

wherein R$_1$ is

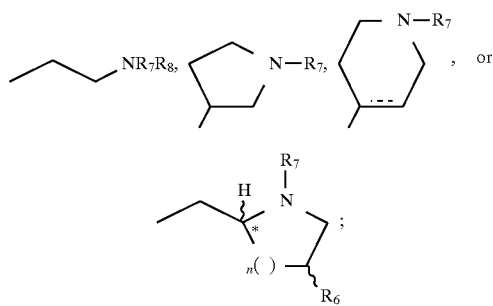

n is 0, 1, or 2; A, B, C, and D are each independently nitrogen or carbon; R$_2$, R$_3$, R$_4$, and R$_5$ are each independently hydrogen, C$_1$ to C$_6$ alkyl, aryl, C$_1$ to C$_3$ alkyl-aryl, halogen, cyano, nitro, —(CH$_2$)$_m$NR$_{14}$R$_{15}$, —(CH$_2$)$_m$OR$_9$, —SR$_9$, —SO$_2$NR$_{14}$R$_{15}$, —(CH$_2$)$_m$NR$_{14}$SO$_2$R$_{15}$, —(CH$_2$)$_m$NR$_{14}$CO$_2$R$_9$, —(CH$_2$)$_m$NR$_{14}$COR$_9$, —(CH$_2$)$_m$NR$_{14}$CONHR$_9$, —CONR$_{14}$R$_{15}$, or —CO$_2$R$_9$; R$_2$ and R$_3$, R$_3$ and R$_4$, or R$_4$ and R$_5$ may be taken together to form a five- to seven-membered alkyl ring, a six-membered aryl ring, a five- to seven-membered heteroalkyl ring having 1 heteroatom of N, O, or S, or a five- to six-membered heteroaryl ring having 1 or 2 heteroatoms of N, O, or S; R$_6$ is hydrogen, —OR$_{10}$, or —NHCOR$_{10}$; R$_7$, R$_8$, R$_{14}$, and R$_{15}$ are each independently hydrogen, C$_1$ to C$_6$ alkyl, —(CH$_2$)$_x$OR$_{11}$, C$_1$ to C$_3$ alkyl-aryl, aryl; R$_7$ and R$_8$ or R$_{14}$ and R$_{15}$ may be taken together to form a three- to six-membered ring; R$_9$ is hydrogen, C$_1$ to C$_6$ alkyl, C$_1$ to C$_3$ alkyl-aryl, or aryl; R$_{10}$ is hydrogen, C$_1$ to C$_6$ alkyl, or C$_1$ to C$_3$ alkyl-aryl; R$_{11}$ is hydrogen, C$_1$ to C$_6$ alkyl, or C$_1$ to C$_3$ alkyl-aryl; m is 0, 1, 2, or 3; x is 2 or 3; a broken line represents an optional double bond; and the above aryl groups and the aryl moieties of the above alkyl-aryl groups are independently phenyl or substituted phenyl, wherein said substituted phenyl may be substituted with one to three of C$_1$ to C$_4$ alkyl, halogen, hydroxy, cyano, carboxamido, nitro, or C$_1$ to C$_4$ alkoxy wherein if any of A, B, C or D is nitrogen, then the corresponding substitutient R$_2$, R$_3$, R$_4$ or R$_5$ does not appear.

2. The compound according to claim 1, wherein R$_1$ is

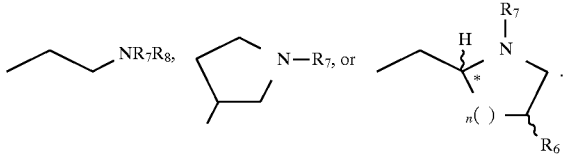

3. A compound according to claim 2, wherein R$_1$ is

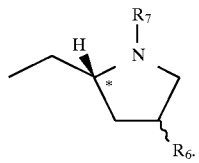

4. A compound according to claim 3, wherein the compound is the cis epimer.

5. A compound according to claim 4, wherein R$_6$ is C$_1$ to C$_3$ alkoxy.

6. A compound according to claim 3, wherein R$_6$ is hydrogen.

7. A compound according to claim 1, wherein A, B, and C are each carbon and D is carbon or nitrogen.

8. A compound according to claim 7, wherein R$_1$ is

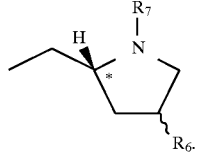

9. A compound according to claim 8, wherein the compound is the cis epimer.

10. A compound according to claim 9, wherein R$_6$ is C$_1$ to C$_3$ alkoxy.

11. A compound according to claim 8, wherein R$_6$ is hydrogen.

12. A compound according to claim 1, said compound being selected from:

5-cyano-1-[3-(N-(2-methoxyethyl)pyrrolidin-2R-ylmethyl)indol-5-yl]-1H-benzimidazole;

5-methoxycarbonyl-1-[3-(N-(2-methoxyethyl)pyrrolidin-2R-ylmethyl)indol-5-yl]-1H-enzimidazole;

5-cyano-1-[3-(4R-methoxypyrrolidin-2R-ylmethyl)indol-5-yl]-1H-benzimidazole;

5-cyano-1-[3-(N-(2-methoxyethyl)-4R-methoxypyrrolidin-2R-ylmethyl)indol-5-yl]-1H-benzimidazole;

5-hydroxymethyl-1-[3-(N-(2-methoxyethyl)pyrrolidin-2R-ylmethyl)indol-5-yl]-1H-benzimidazole;

5-cyano-1-[3-(pyrrolidin-2R-ylmethyl)indol-5-yl]-1H-benzimidazole;

1-[3-(N-cyclopropylmethly)pyrrolidin-2R-ylmethyl)indol-5-yl]-3H-imidazo[4,5-b]pyridine;

1-[3-(pyrrolidin-2R-ylmethyl)indol-5-yl]-3H-imidazo[4,5-b]pyridine;

5-cyano-1-[3-(N-methylpyrrolidin-2R-ylmethyl)indol-5-yl]-1H-benzimidazole;

5-cyano-1-[3-(N-cyclopropylmethyl)pyrrolidin-2R-ylmethyl)indol-5-yl]-1H-benzimidazole;

1-[3-(N-methylpyrrolidin-2R-ylmethyl)indol-5-yl]-1H-benzimidazole;

4-methyl-1-[3-(N-methlypyrrolidin-2R-ylmethyl)indol-5-yl]-1H-benzimidazole;

1-[3-(N-methylpyrrolidin-2R-ylmethyl)indol-5-yl]-3H-imidazo[4,5-b]pyridine;

6-methoxy-1-[3-(N-methylpyrrolidin-2R-ylmethyl)indol-5-yl]-3H-imidazo[4,5-b]pyridine;

1-[3-(N-methylpyrrolidin-2R-ylmethyl)indol-5-yl]-5-trifluoromethyl-1H-benzimidazole;

1-[3-(2-N,N-dimethylaminoethyl)indol-5-yl]-3H-imidazo[4,5-b]pyridine;

1-[3-(2-aminoethyl)indol-5-yl]-3H-imidazo[4,5-b]pyridine;

1-[3-(N-methylpyrrolidin-2R-ylmethyl)indol-5-yl]-5-phenyl-1H-benzimidazole;

6,7-dichloro-1-[3-(N-methylpyrrolidin-2R-ylmethyl)indol-5-yl]-1H-benzimidazole;

1-[3-(piperid-4-yl)indol-5-yl]-3H-imidazo[4,5-b]pyridine;

1-[3-(N-methylpyrrolidin-3-yl)indol-5-yl]-3H-imidazo[4,5-b]pyridine, 5-chloro-1-[3-(N-methylpyrrolidin-2R-ylmethyl)indol-5-yl]-1H-benzimidazole;

6-chloro-1-[3-(N-methylpyrrolidin-2R-ylmethyl)indol-5-yl]-1H-benzimidazole;

7-chloro-1-[3-(N-methylpyrrolidin-2R-ylmethyl)indol-5-yl]-1H-benzimidazole;

5-aminomethyl-1-[3-(N-(2-methoxyethyl)pyrrolidin-2R-ylmethyl)indol-5-yl]-1H-benzimidazole;

5-acetylaminomethyl-1-[3-(N-(2-methoxyethyl)pyrrolidin-2R-ylmethyl)indol-5-yl]-1H-benzimidazole;

5-cyano-1-[3(piperid-4-yl)indol-5-yl]-1H-benzimidazole;

5-cyano-1-[3-(1,2,5,6-tetrahydropyrid-4-yl)indol-5-yl]-1H-benzimidazole;

N-phenyl-N'-[3-(N-(2-methoxyethyl)pyrrolidin-2R-ylmethyl)indol-5-yl]-1H-benz[b]imidazyl]methylurea;

5-cyano-1-[3-(N-methylpyrrolidin-3-yl)indol-5-yl]-1H-benzimidazole;

5-benzoylaminomethyl-1-[3-(N-(2-methoxyethyl)pyrrolidin-2R-ylmethyl)indol-5-yl]-1H-benzimidazole;

5-aminomethyl-1-[3-N-methylpyrrolidin-2R-ylmethyl)indol-5-yl]-1H-benzimidazole;

5-cyano-1-[3-(N-methylpyrrolidin-2R-ylmethyl)indol-5-yl]-1H-pyrido[4,5-b]imidazole; and 4-methyl-1-[3-(N-methylpyrrolidin-2R-ylmethyl)indol-5-yl]-1H-pyrido[4,5-b]imidazole.

13. A pharmaceutical composition for treating a condition selected from hypertension, depression, anxiety, eating disorders, obesity, drug abuse, cluster headache, migraine, pain, and chronic paroxysmal hemicrania and headache associated with vascular disorders comprising an amount of a compound or pharmaceutically acceptable salt thereof according to claim 1 effective in treating such condition and a pharmaceutically acceptable carrier.

14. A pharmaceutical composition for treating disorders arising from deficient serotonergic neurotransmission comprising an amount of a compound or phamaceutically acceptable salt thereof according to claim 1 effective in treating such a disorder and a pharmaceutically acceptable carrier.

15. A method for treating a condition selected from hypertension, depression, anxiety, eating disorders, obesity, drug abuse, cluster headache, migraine, pain, and chronic paroxysmal hemicrania and headache associated with vascular disorders comprising administering to a mammal requiring such treatment an amount of a compound according to claim 1 effective in treating such condition.

16. A method for treating disorders arising from deficient serotonergic neurotransmission comprising administering to a mammal requiring such treatment an amount of a compound according to claim 1 effective in treating such condition.

17. A compound of the formula

IV wherein $R_{12}$ is n is 0, 1, or 2; A, B, C, and D are each independently nitrogen or carbon; $R_2$, $R_3$, $R_4$, and $R_5$ are each independently hydrogen, $C_1$ to $C_6$ alkyl, aryl, $C_1$ to $C_3$ alkyl-aryl, halogen, cyano, nitro, —$(CH_2)_m NR_{14}R_{15}$, —$(CH_2)_m OR_9$, —$SR_9$, —$SO_2NR_{14}R_{15}$, —$(CH_2)_m NR_{14}SO_2R_{15}$, —$(CH_2)_m NR_{14}CO_2R_9$, —$(CH_2)_m NR_4COR_9$, —$(CH_2)_m NR_{14}CONR_{14}R_{15}$, or —$CO_2R_9$; $R_2$ and $R_3$, $R_3$ and $R_4$, or $R_4$ and $R_5$ may be taken together to form a five to seven-membered alkyl ring, a six-membered aryl ring, a five- to seven-membered heteroalkyl ring having 1 heteroatom of N, O, or S, or a five- to six-membered heteroaryl ring having 1 or 2 heteroatoms of N, O, or S; $R_6$ is hydrogen, —$OR_{10}$, or —$NHCOR_{10}$; $R_7$, $R_{14}$, and $R_{15}$ are each independently hydrogen, $C_1$ to $C_6$ alkyl, —$(CH_2)_xOR_{11}$, $C_1$ to $C_3$ alkyl-aryl, or aryl; $R_{14}$ and $R_{15}$ may be taken together to form a three- to six-membered ring; $R_9$ is hydrogen, $C_1$ to $C_6$ alkyl, $C_1$ to $C_3$ alkyl-aryl, or aryl; $R_{10}$ is hydrogen, $C_1$ to $C_6$ alkyl, or $C_1$ to $C_3$ alkyl-aryl; $R_{11}$ is hydrogen, $C_1$ to $C_6$ alkyl, or $C_1$ to $C_3$ alkyl-aryl; $R_{13}$ is —$COR_{16}$, —$CO_2R_{16}$, or —$CH_2Ph$; $R_{16}$ is $C_1$ to $C_6$ alkyl, $C_1$ to $C_3$ alkyl-aryl, or aryl; m is 0, 1, 2, or 3; x is 2 or 3; a broken line represents an optional double bond; and the above aryl groups and the aryl moieties of the above alkyl-aryl groups are independently phenyl or substituted phenyl, wherein said substituted phenyl may be substituted with one to three of $C_1$ to $C_4$ alkyl, halogen, hydroxy, cyano, carboxamido, nitro, or $C_1$ to $C_4$ alkoxy wherein if any of A, B, C or D is nitrogen, then the corresponding substitutient $R_2$, $R_3$, $R_4$ or $R_5$ does not appear.

18. A compound according to claim 17, wherein $R_{12}$ is

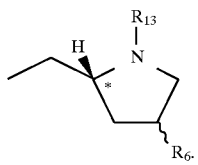

19. A compound according to claim 18, wherein the compound is the cis epimer.

20. A compound according to claim 19, wherein $R_6$ is $C_1$ to $C_3$ alkoxy.

21. A compound according to claim 18, wherein $R_6$ is hydrogen.

* * * * *